United States Patent
Franz et al.

(10) Patent No.: US 10,991,118 B2
(45) Date of Patent: Apr. 27, 2021

(54) DEVICE, PROCESS AND COMPUTER PROGRAM FOR DETECTING OPTICAL IMAGE DATA AND FOR DETERMINING A POSITION OF A LATERAL LIMITATION OF A PATIENT POSITIONING DEVICE

(71) Applicant: Drägerwerk AG & Co. KGaA, Lübeck (DE)

(72) Inventors: Frank Franz, Stockelsdorf (DE); Stefan Schlichting, Lübeck (DE); Jasper Diesel, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days.

(21) Appl. No.: 16/471,322

(22) PCT Filed: Dec. 12, 2017

(86) PCT No.: PCT/EP2017/082340
§ 371 (c)(1),
(2) Date: Jun. 19, 2019

(87) PCT Pub. No.: WO2018/114454
PCT Pub. Date: Jun. 28, 2018

(65) Prior Publication Data
US 2020/0105010 A1 Apr. 2, 2020

(30) Foreign Application Priority Data
Dec. 20, 2016 (DE) .................... 10 2016 015 121.8

(51) Int. Cl.
*G06T 7/70* (2017.01)
*G16H 50/30* (2018.01)
(Continued)

(52) U.S. Cl.
CPC .............. *G06T 7/70* (2017.01); *G06K 9/6228* (2013.01); *G06T 7/60* (2013.01); *G08B 21/043* (2013.01);
(Continued)

(58) Field of Classification Search
CPC ............. G06T 7/70; G06T 2207/10028; G06T 2207/30004; G06T 7/60; G06T 7/74;
(Continued)

(56) References Cited

U.S. PATENT DOCUMENTS

2012/0075464 A1\* 3/2012 Derenne ................ A61B 5/112
348/135
2012/0223821 A1 9/2012 Collins, Jr.
(Continued)

FOREIGN PATENT DOCUMENTS

| EP | 1504427 B1 | 3/2011 |
|---|---|---|
| WO | 2015055312 A1 | 4/2015 |
| WO | 015125544 A1 | 8/2015 |

OTHER PUBLICATIONS

Bed angle detection in hospital rooms using Microsoft Kinect V2; Jun. 2016 (Year: 2016).\*
(Continued)

*Primary Examiner* — Hirdepal Singh
(74) *Attorney, Agent, or Firm* — McGlew and Tuttle, P.C.

(57) ABSTRACT

Exemplary embodiments provide a device (10), a process and a computer program for detecting optical image data of a patient positioning device (100). The device (10) is configured to detect optical image data of a patient positioning device (100) and to determine a position of at least one lateral limitation (110) of the patient positioning device (100) based on the image data. The device (10) is configured to determine at first a position of art least one partial segment (120) of the patient positioning device (100) based on the
(Continued)

image data, and to determine the position of the at least one lateral limitation (110) of the patient positioning device (100) based on the position of the at least one partial segment (120).

16 Claims, 18 Drawing Sheets

(51) Int. Cl.
    *G16H 40/63*     (2018.01)
    *G06K 9/62*     (2006.01)
    *G06T 7/60*     (2017.01)
    *G08B 21/04*     (2006.01)

(52) U.S. Cl.
CPC ......... *G08B 21/0476* (2013.01); *G16H 40/63* (2018.01); *G16H 50/30* (2018.01); *G06T 2207/10028* (2013.01); *G06T 2207/30004* (2013.01)

(58) Field of Classification Search
CPC ........ G16H 50/30; G16H 40/67; G16H 40/63; G06K 9/6228; G08B 21/043; G08B 21/0476
USPC ...................................... 340/573.1
See application file for complete search history.

(56) References Cited

U.S. PATENT DOCUMENTS

| | | | |
|---|---|---|---|
| 2015/0257952 A1* | 9/2015 | Zerhusen | A61G 7/051 340/12.5 |
| 2015/0293600 A1* | 10/2015 | Sears | H04N 13/271 345/156 |
| 2016/0034773 A1 | 2/2016 | Goncalves | |
| 2016/0193095 A1* | 7/2016 | Roussy | A61G 7/0514 5/11 |
| 2017/0076042 A1* | 3/2017 | Katz | G06K 9/00355 |
| 2017/0169691 A1* | 6/2017 | Kirenko | A61B 5/1117 |
| 2019/0228866 A1* | 7/2019 | Weffers-Albu | G16H 10/60 |

OTHER PUBLICATIONS

Kittipanya-Ngam et al., "Bed Detection for Monitoring System in Hospital Wards," 34th Annual International Conference of the IEEE EMBS, San Diego, California USA, Aug. 28-Sep. 1, 2012; pp. 5887-5890.
Liu et al., "Bed angle detection in hospital room using Microsoft Kinect V2," 2015 IEEE 13th international Conference on Wearable and Implantable Body Sensor Networks (NSN), IEEE, Jun. 14, 2016 pp. 277-280.
Besl, P. J. (1992), "Method for registration of 3-D shapes", In Robotics-DL tentative (pp. 586-606).
Fischler, M. A. (1981), "Random sample consensus: a paradigm for model fitting with applications to image analysis and automated cartography", Communications of the ACM, pp. 381-395.
Hartman, F. (2011), "Robotersteuerung durch Gesten" [Robot Control by Gestures], Master Thesis at the University of Lübeck.
Shapiro, L., & Stockman, G. (2001), "Computer Vision", Prentice-Hall.
Bron, C., & Kerbosch, J. (1973), "Algorithm 457: finding all cliques of an undirected graph, Communications of the ACM", pp. 575-577.
Canny, J. (1986), "A Computational Approach to Edge Detection", IEEE Transactions on Pattern Analysis and Machine Intelligence.
Capezuti, E., Wagner, L., & Brush, B. (2007), "Consequences of an intervention to reduce restrictive side rail use in nursing homes", Journal of the American Geriatrics Society, pp. 334-341.
Dalal, N., & Triggs, B. (2005), "Histograms of Oriented Gradients for Human Detection", IEEE Computer Society Conference on Computer Vision and Pattern Recognition.
Duda, R., & Hart, P. E. (1972), "Use of the Hough Transformation to Detect Lines and Curves in Pictures", Comm. ACM, pp. 11-15.
Hartman, F. (2011), „Robotersteuerung durch Gesten [Robot Control by Gestures], University of Lübeck.
Jolliffe, I. T. (2002), "Principal Component Analysis", Springer.
Talerico, K. A., & Capezuti, E. (2001), "Myths and Facts About Side Rails: Despite ongoing debates about safety and efficacy, side rails are still a standard component of care in many hospitals, so how do you determine their safe use?", AJN The American Journal of Nursing, pp. 43-48.
Viola, P., & Jones, M. (2001), "Rapid object detection using a boosted cascade of simple features", Conference on Computer Vision and Pattern Recognition 2001.

* cited by examiner

DEVICE, PROCESS AND COMPUTER PROGRAM FOR DETECTING OPTICAL IMAGE DATA AND FOR DETERMINING A POSITION OF A LATERAL LIMITATION OF A PATIENT POSITIONING DEVICE

CROSS REFERENCE TO RELATED APPLICATIONS

This application is a United States National Phase Application of International Application PCT/EP2017/082340 filed Dec. 12, 2017, and claims the benefit of priority under 35 U.S.C. § 119 of German Application 10 2016 015 121.8, filed Dec. 20, 2016, the entire contents of which are incorporated herein by reference.

TECHNICAL FIELD

Exemplary embodiments pertain to a device, to a process and to a computer program for determining a position of a lateral limitation of a patient positioning device, especially but not exclusively to a concept for the automated determination of the position of a lateral limitation of a hospital bed based on optical image data.

TECHNICAL BACKGROUND

Various concepts, which estimate a position, posture or reclining position or position/pose of a patient on a hospital bed, are known in the conventional technology, motivated, for example, by the existence of unfavorable postures, which may adversely affect a healing process or may represent a health risk. This may also include the case in which a patient remains in a position or maintains a posture over a certain time period. The posture or pose of a patient confined to a hospital bed depends on the setting or configuration of the hospital bed being used. Such patients are often in situations, for example, in accommodations, wards or hospital rooms intended for this purpose, in which corresponding monitoring, documentation and warning mechanisms are then provided in order to avoid critical or false postures. Facilities for assisted living, care facilities, home care facilities, nursing homes, hospitals and intensive care units are some examples.

Lateral limitations that may be present, e.g., bed rails, safety barriers, limitations, etc., which are mounted at positioning devices for patients, and which are used, for example, to secure the patients against falling out or falling down, play an important role in this connection.

In the area of care, there are adjustable or configurable hospital beds or nursing beds, which are available to patients at home or even in corresponding facilities, such as hospitals. The available hospital beds are usually unable to provide information on a current configuration, or they use manufacturer-specific protocols or protocols of their own for this. The prevention of falling and entrapment is of great interest in medical care. Persons who are especially prone to this type of accidents often suffer from a disease, such as Alzheimer's disease, are physically impaired or under the influence of potent drugs. Uncoordinated, unconscious to conscious, autoaggressive actions of the patients occur especially in intensive care units during delirium ("transit syndrome"), which lead time and time again to a fall of the already severely ill patient from the patient positioning device (PPD). This may have drastic consequences ranging from severe injuries to death.

In addition to being in intensive care units, patients are in hospitals, retirement homes, psychiatric institutions or other care facilities. The health care staff can take various countermeasures, which are to reduce the risk of an accident. These include especially the constant monitoring and correct assessment of the patient, a safe environment and various aids, such as bed rails at PPDs and alternatives thereof.

Further background information can be found in the following documents:

Besl, P. J. (1992), "Method for registration of 3-D shapes", In Robotics-DL tentative (pp. 586-606),
Fischler, M. A. (1981), "Random sample consensus: a paradigm for model fitting with applications to image analysis and automated cartography", Communications of the ACM, pp. 381-395,
Hartman, F. (2011), "Robotersteuerung durch Gesten" [Robot Control by Gestures], Master Thesis at the University of Lübeck,
Kong, T., & Rosenfeld, A. (1996), "Topological Algorithms for Digital Image Processing", Elsevier Science, Inc.,
Shapiro, L., & Stockman, G. (2001), "Computer Vision", Prentice-Hall,
Bron, C., & Kerbosch, J. (1973), "Algorithm 457: finding all cliques of an undirected graph, Communications of the ACM", pp. 575-577,
Canny, J. (1986), "A Computational Approach to Edge Detection", IEEE Transactions on Pattern Analysis and Machine Intelligence,
Capezuti, E., Wagner, L., & Brush, B. (2007), "Consequences of an intervention to reduce restrictive side rail use in nursing homes", Journal of the American Geriatrics Society, pp. 334-341,
Dalal, N., & Triggs, B. (2005), "Histograms of Oriented Gradients for Human Detection", IEEE Computer Society Conference on Computer Vision and Pattern Recognition,
Duda, R., & Hart, P. E. (1972), "Use of the Hough Transformation to Detect Lines and Curves in Pictures", Comm. ACM, pp. 11-15,
Hartman, F. (2011), "Robotersteuerung durch Gesten" [Robot Control by Gestures], University of Lübeck,
Jolliffe, I. T. (2002), "Principal Component Analysis", Springer,
Soille, P. (1999), "Morphological Image Analysis: Principles and Applications", Springer-Verlag,
Talerico, K. A., & Capezuti, E. (2001), "Myths and Facts About Side Rails: Despite ongoing debates about safety and efficacy, side rails are still a standard component of care in many hospitals, so how do you determine their safe use?", AJN The American Journal of Nursing, pp. 43-48, and
Viola, P., & Jones, M. (2001), "Rapid object detection using a boosted cascade of simple features", CONFERENCE ON COMPUTER VISION AND PATTERN RECOGNITION 2001.

SUMMARY

Therefore, there is a need for developing an improved concept for detecting a bed configuration. This need is met by exemplary embodiments of a device, of a process and of a computer program according to the invention.

Some exemplary embodiments can automatically detect, for example, the setting of bed rails (and hence also the use thereof) in order to assist, for example, the documentation or to activate further monitoring systems, which are indicated in case of the use of bed rails. This is accomplished by optical image data of a patient positioning device being detected, by a position of at least one partial segment of the patient positioning device and, based on this, a position of a lateral limitation of the patient positioning device being further determined. The situation of the patient can be inferred from the position of the lateral limitation. For example, safety risks can be inferred if a lateral limitation is not set high enough.

The proposed solution is therefore advantageous especially because a risk for the patient can be inferred from the position of the at least one partial segment and the lateral limitation. In other words, exemplary embodiments of the present invention are based on the idea of analyzing and processing optically detected image data of a patient positioning device and of inferring from this the position of at least one partial segment and of a lateral limitation. Exemplary embodiments provide a device for detecting optical image data of a patient positioning device and for determining a position of at least one lateral limitation of the patient positioning device based on the image data. The device is configured to determine first a position of at least one partial segment of the patient positioning device based on the image data. The device is further configured to determine the position of the at least one lateral limitation of the patient positioning device on the basis of the position of the at least one partial segment. Exemplary embodiments can provide an improved concept for the observation, the safety monitoring or the documentation of the configurations of patient positioning devices by the determination of the position of the lateral limitation from the image data. In some exemplary embodiments, the device may further have an interface for outputting information on the position of the at least one lateral limitation. For example, the information on the position of the lateral limitation can thus be made available, e.g., for displaying to the health care staff, for further data processing or for automated monitoring.

In some exemplary embodiments, the device may, moreover, comprise a detection device for detecting the optical image data of the patient positioning device. The detection device may have one or more sensors, which is/are configured to detect a three-dimensional point cloud as image data. The image data can thus be detected independently from the patient positioning devices, so that any desired patient positioning devices can be used. Moreover, a sensor system arranged at the patient positioning device may be dispensed with. Limitations for patients or the staff due to additional components or wiring to a patient positioning device can thus be avoided.

In further exemplary embodiments, the device may further comprise a determination device, which is configured to determine the position of the at least one partial segment of the patient positioning device based on the image data. The determination device may further be configured to determine a size and a position of a reclining surface of the patient positioning device based on the position of the at least one partial segment of the patient positioning device. Exemplary embodiments can thus also include information on the reclining surface, e.g., the orientation or configuration thereof, in the further consideration.

The determination device may be configured, for example, to further determine two long sides of the patient positioning device, and to at least partially exclude from the image data pixels that do not belong to the at least one lateral limitation of the patient positioning device. Exemplary embodiments can thus make an effective data processing possible. The determination device may be configured, moreover, to limit, furthermore, the image data to pixels of a long side of the patient positioning device. Detection of the lateral limitations can thus be performed for, for example, two long sides separately and thus facilitate a detection. The determination device may further be configured to project the image data onto a lateral plane of the patient positioning device and to obtain a projected image. The determination device may then be configured to determine lateral limitation candidates in the projected image by means of an object detection. Exemplary embodiments can thus provide an effective algorithm for analyzing the image data. The determination device may be configured in further exemplary embodiments to analyze the lateral limitation candidates and to determine the position of the at least one lateral limitation based on the analyzed lateral limitation candidates. The reliability of the detection of the lateral limitation can be measured by the analysis and also included in a consideration.

The determination device may be configured in some exemplary embodiments to determine safety information on a configuration of the patient positioning device on the basis of the position of the at least one lateral limitation. The safety information may then be used to assess a situation for the patient. For example, the determination device may be configured to document the safety information via a storage device and/or to output the safety information via a display device. Exemplary embodiments can thus make the safety information available. The determination device may also be configured in at least some exemplary embodiments to output alarm information based on the safety information when the configuration of the patient positioning device is below a safety level. An alarm can then be generated for health care staff. The safety level of the patient positioning device may be based, for example, on a relative position of the at least one partial segment in relation to the at least one lateral limitation. The relative position of the at least one partial segment or of a reclining surface arranged parallel thereto relative to the lateral limitation may be, for example, an indicator of a risk of slipping or rolling or falling out on the side. The safety level may be an indicator of how high a risk of a patient falling out of the patient positioning device is in the particular configuration of the patient positioning device. As a result, a documentation or an early warning can, in turn, be established for the health care staff. The safety level may represent, for example, an indicator of a mean level of the lateral limitation above a reclining surface above the at least one partial segment.

The determination device may also be configured in further exemplary embodiments to determine the position of at least two and, for example, also four, partial segments of the patient positioning device. Exemplary embodiments can thus make safety information available for different configurations even in case of more complicated patient positioning devices.

Moreover, exemplary embodiments provide a process for detecting optical image data of a patient positioning device and for determining a position of at least one lateral limitation of the patient positioning device based on the image data. The process comprises a determination of a position of at least one partial segment of the patient positioning device based on the image data. The process further comprises a determination of the position of the at least one lateral limitation of the patient positioning device based on the position of the at least one partial segment.

Another exemplary embodiment is a program or computer program with a program code for executing a process being described herein, if the program code is executed on a computer, on a processor or on a programmable hardware component.

Further advantageous embodiments will be described in more detail below on the basis of the exemplary embodiments shown in the drawings, to which exemplary embodiments the invention is not limited. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
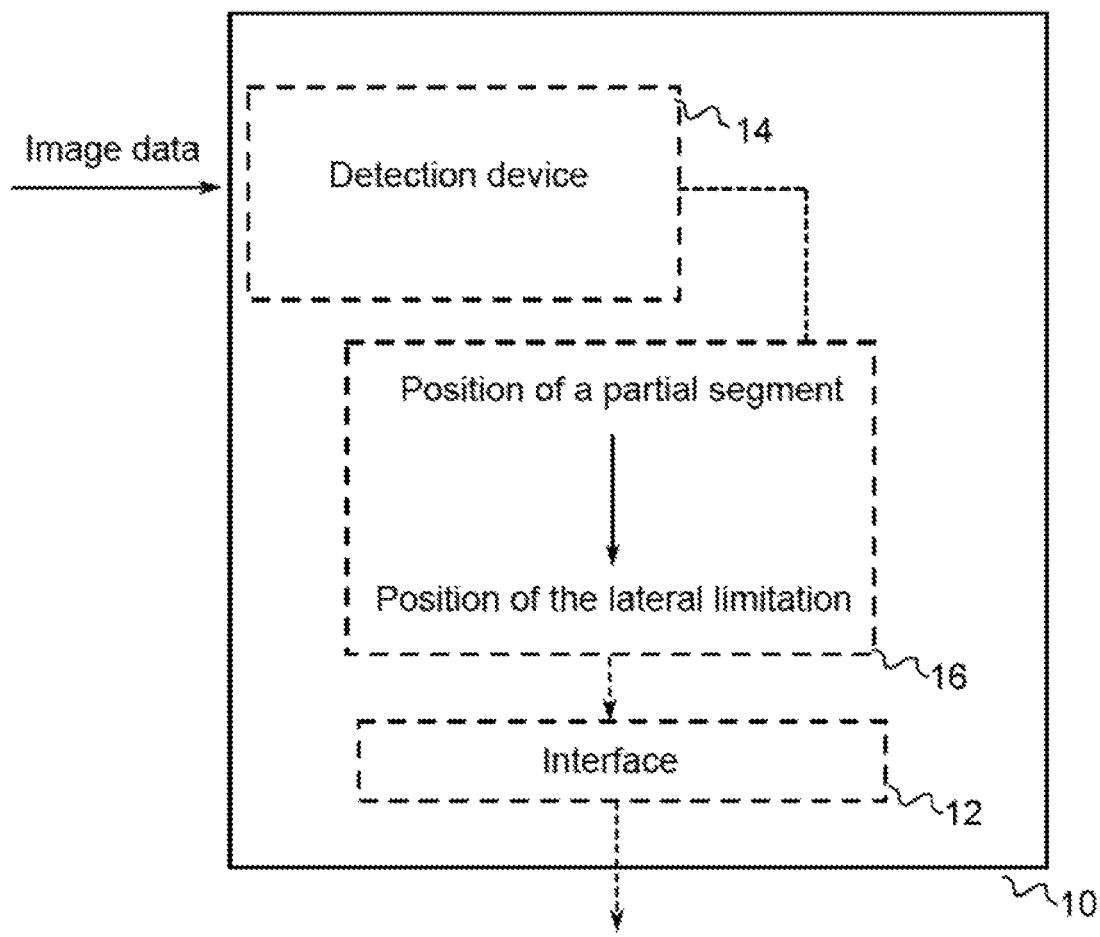
FIG. 1 is a schematic view of an exemplary embodiment of a device for detecting optical image data of a patient positioning device and for determining a position of at least one lateral limitation.

Referring to the drawings, different exemplary embodiments will now be described in more detail with reference to the attached drawings, in which some exemplary embodiments are shown.

In the following description of the attached figures, which show only some examples of exemplary embodiments, identical reference numbers may designate identical or comparable components. Further, summary reference numbers may be used for components and objects that are present as a plurality of components and objects in an exemplary embodiment or in a drawing but are described jointly in respect to one or more features. Components or objects that are described with identical or summary reference numbers may have an identical configuration in respect to individual features, a plurality of features or all features, for example, their dimensions, but they may possibly also have different configurations unless something different appears explicitly or implicitly from the description. Optional components are represented by broken lines or arrows in the figures.

Even though exemplary embodiments may be modified and varied in different ways, exemplary embodiments are shown in the figures as examples and will be described in detail herein. It should, however, be made clear that exemplary embodiments are not intended to be limited to the respective disclosed forms, but exemplary embodiments shall rather cover all functional and/or structural modifications, equivalents and alternatives, which are within the scope of the present invention. Identical reference numbers designate identical or similar elements in the entire description of the figures.

It should be noted that an element that is described as being "connected" or "coupled" with another element may be connected or coupled directly with the other element or elements located between them may be present. If, by contrast, an element is described as being "connected directly" or "coupled directly" with another element, no elements located between them are present. Other terms, which are used to describe the relationship between elements, shall be interpreted in a similar manner (e.g., "between" versus "directly between," "adjoining" versus "directly adjoining," etc.).

The terminology that is used here is used only to describe certain exemplary embodiments and shall not limit the exemplary embodiments. As being used here, the singular forms "a," "an" and "the" shall also include the plural forms unless the context unambiguously indicates something different. It should further be made clear that such terms as, e.g., "contains," "containing," "has," "comprises," "comprising" and/or "having," as used here, indicate the presence of said features, integers, steps, work processes, elements and/or components, but they do not rule out the presence or the addition of a feature or of one or more features, integers, steps, work processes, elements, components and/or groups thereof.

Unless defined otherwise, all the terms being used here (including technical and scientific terms) have the same meaning that a person having ordinary skill in the art to which the exemplary embodiments belong attributes to them. It should further be made clear that terms, e.g., those that are defined in generally used dictionaries, are to be interpreted such as if they had the meaning that is consistent with their meaning in the context of the relevant technology, and they are not to be interpreted in an idealized or excessively formal sense, unless this is expressly defined here.

FIG. 1 shows an exemplary embodiment of a device 10 for detecting optical image data of a patient positioning device and for determining a position of at least one lateral limitation of the patient positioning device based on the image data. The device 10 is configured to determine first a position of at least one partial segment of the patient positioning device based on the image data, and to determine the position of the at least one lateral limitation of the patient positioning device based on the position of the at least one partial segment. Optional components are shown by broken lines in the figures.

Figure 2:
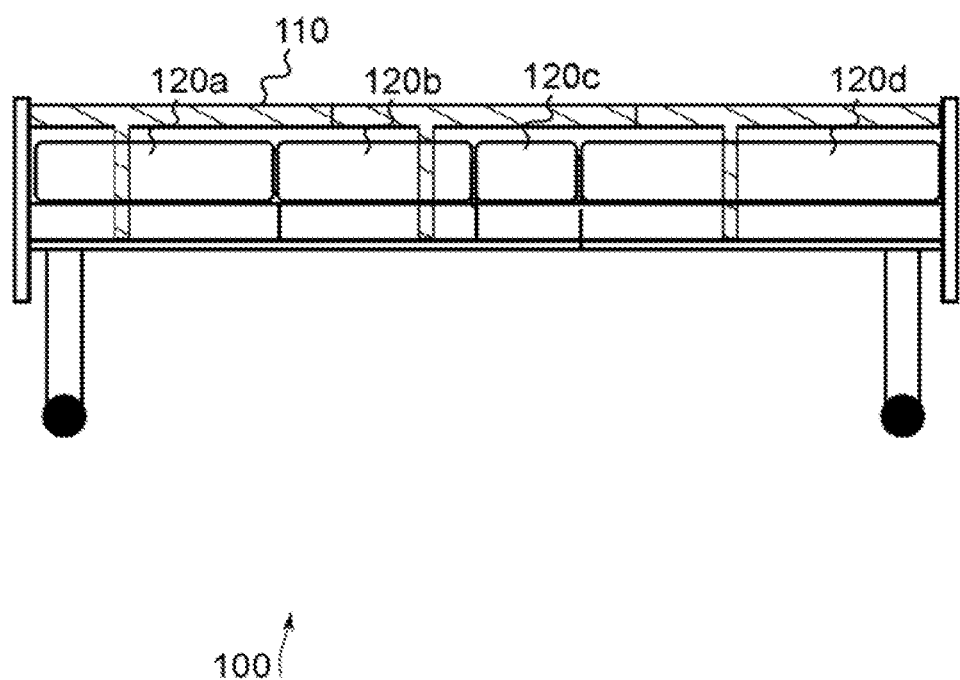
FIG. 2 is a schematic view of a hospital bed as a patient positioning device with four segments in one exemplary embodiment.

In exemplary embodiments, the patient positioning device 100 may have one or more segments 120. FIG. 2 shows a hospital bed as an example of a patient positioning device 100 with four segments 120a, 120b, 120c and 120d. A patient positioning device 100 should here and hereinafter be defined, for example, as an adjustable hospital bed, an operating table, a daybed, a stretcher, a transfer table, a patient chair, a wheelchair, etc., i.e., a device that is suitable for positioning, for bedding, for supporting, possibly for transporting, etc., persons, patients or persons in need of care. Some exemplary embodiments will be considered below based on the example of a hospital bed. This hospital bed is considered and intended to represent any desired patient positioning devices.

Figure 3:
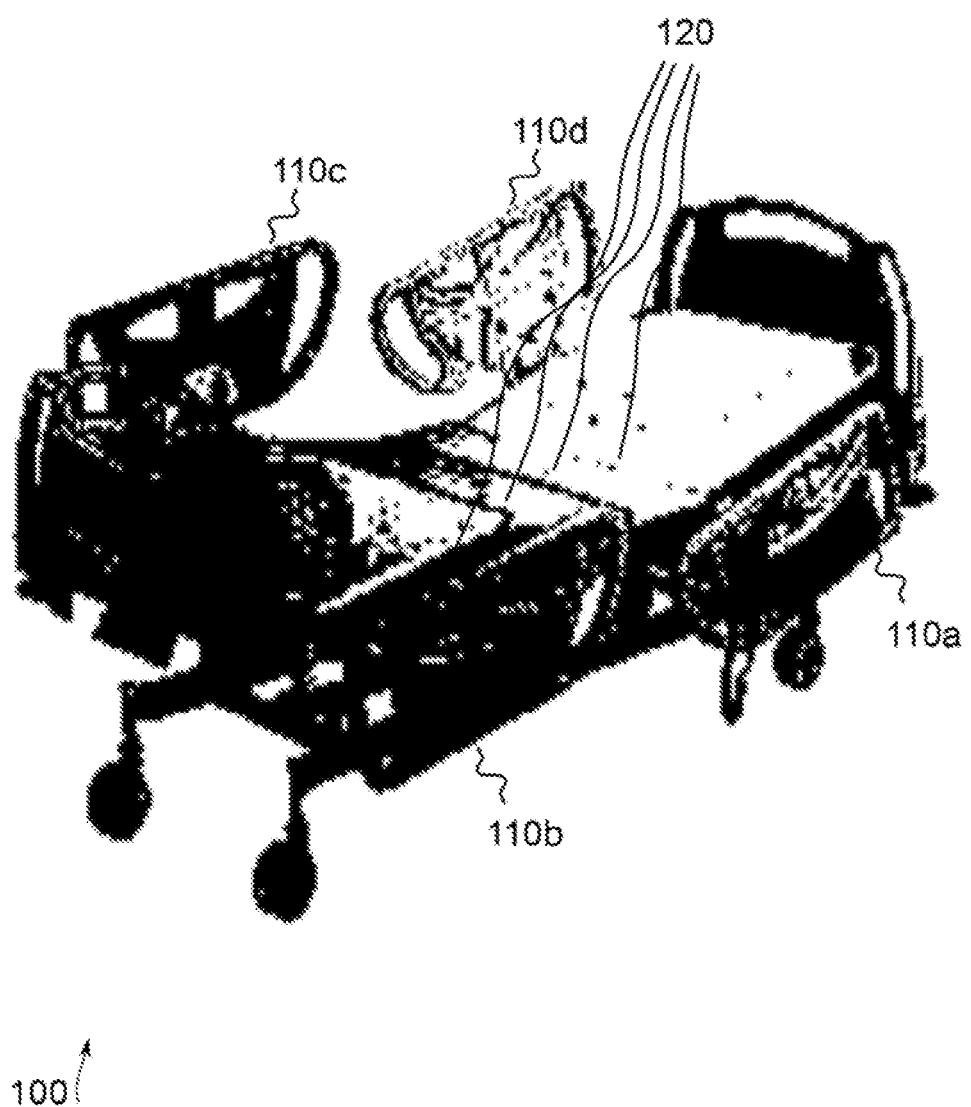
FIG. 3 is a schematic perspective view of a hospital bed as a patient positioning device with four lateral limitations or bed rails.

FIG. 3 shows a hospital bed as a patient positioning device 100 with four lateral limitations or bed rails 110a, 110b, 110c, 110d and with a plurality of partial segments 120. As is shown in FIGS. 2 and 3, the segments 120 may be intended for different functions, for example, for supporting the foot, leg, trunk, back, head, etc., as well as be divided into areas, e.g., a sitting area and a reclining area. The partial segments 120, 120a, 120b, 120c, 120d in FIG. 2 are associated at least partially with segments of a reclining and/or sitting area of the patient positioning device 100. Instead of the hospital bed, any other desired patient positioning device 100 having corresponding segments 120 may also be considered in further exemplary embodiments. The partial segments 120a, 120b, 120c, 120d may be able to be configured or adjusted and therefore assume different positions in relation to one another or also relative to a bed frame, cf. FIGS. 2 and 3.

In the exemplary embodiment shown, the mattress of the bed is divided into the four segments 120a, 120b, 120c, 120d, which can be configured. The lateral limitations 110 are shown in FIG. 2 as raised bed rails, which offer at least some safety to a patient against rolling out at least when the partial segments 120a, 120b, 120c, 120d are in a flat position. The position of a segment 120, 120a, 120b, 120c, 120d or of a lateral limitation, an orientation, direction, relative alignment and position of such segment or lateral limitation in relation to at least one other partial segment, e.g., the angle at which the longitudinal or transverse axes intersect, the relative alignment and position in relation to a reference object, e.g., floor, and the axis of the patient positioning device should here and hereinafter be defined as information that informs the health care staff on whether a setting of the patient positioning device or of a lateral limitation shall be changed in the given state of a patient located thereon, etc. The determination of information on the position is consequently carried with the aim of obtaining information on the setting or configuration of the patient positioning device 100 in order to then be able, for example, to document this and/or also to assess whether a change should be made in the setting. The position of the at least one partial segment 120 and of the at least one lateral limitation 110 can thus refer to any one-, two- or three-dimensional information, which makes it possible to infer the setting or configuration of the at least one partial segment 120 or of the at least one lateral limitation 110, e.g., in the form of angles, straight lines, planes, etc.

FIG. 3 shows different positions of lateral limitations 110a, 110b, 110c and 110d in exemplary embodiments. The configurations are exemplary configurations of adjustable lateral limitations, which number four in this exemplary embodiment.

FIG. 1 shows, moreover, that the device 10 may further have in some exemplary embodiments an interface 12 for outputting information on the position of the at least one lateral limitation 110. The interface 12 may be coupled with a determination device 16 explained further below. For example, information on the configuration/position of the at least one partial segment 120 and/or of the lateral limitation 110 (e.g., angle, angle of intersection, information derived therefrom, etc.) and/or information on the reliability of this information can be communicated via the interface 12 to other components, e.g., for subsequent further processing of the image data, for example, to a display or to a monitor, to a display device, to a storage device, to an alarm generation device or to a documentation system.

The interface 12 may correspond, for example, to one or more inputs and/or to one or more outputs for receiving and/or transmitting information, e.g., in digital bit values, analog signals, magnetic fields, based on a code, within a module, between modules, or between modules of different entities. The interface 12 may, however, also correspond to an input interface 12, such as a control panel, a switch or rotary switch, a button, a touch-sensitive screen (also called "touchscreen" in English), etc. The interface 12 thus makes it possible to record, possibly also to receive or to input, information, for example, on whether a determination of the positions of the partial segments shall be carried out.

PPDs 100 are used in many medical fields, such as in hospitals (e.g., in an emergency room admission unit, recovery room, hospital room, intensive care unit), in the ambulance service or in retirement homes and in home care. They are characterized, in general, in that they offer the patient a reclining surface or sitting surface. Special requirements, which are specially tailored to the needs of patients, are often imposed on PPDs 100. Thus, the reclining surface can frequently be configured, because it comprises different (PPD) segments 120, 120a, 120b, 120c, 120d, which are adjustable in relation to one another. The determination device 16 may be configured to determine the position of at least one partial segment 120 of the patient positioning device 100. Exemplary embodiments in which there are four partial segments 120a-d will be considered below, but more or fewer partial segments 120 may also occur in other exemplary embodiments.

Such an example can be seen in FIG. 2. The head part of the reclining surface can be raised here and the segments 120c, 120d of the leg part can be adjusted such that the patient can bend his or her legs. The position of a patient can thus be influenced considerably, which can increase comfort, minimize risks and improve therapeutic results. Furthermore, PPDs 100 can as a whole often be adjusted vertically and tilted to a certain degree.

Many PPDs 100 are additionally equipped with lateral limitations 110, mostly on both sides. They shall protect the patient and prevent rolling/falling out of the PPD. The probably most frequent form of lateral limitation is the bed rail (or also "bed side supports" or "bed side parts"), as it is also shown in FIGS. 2 and 3. Bed rails have been used to prevent falls for the past 70 years or so. Possible embodiments often differ in whether they are present contiguously on both sides of the bed or whether two bed rails, which are separated from one another, are placed on each bed side. An example of the former variant can be seen in FIG. 2, and an example of the latter is shown in FIG. 3. The bed rails are usually fastened either directly to the bed frame on the side or to one of the PPD segments 120. They are vertically adjustable up and down, potentially also continuously to a setting in between.

The bed rails are two-part bed rails per side in the exemplary embodiment according to FIG. 3, and they are attached to the PPD segments 120. They are raised on the left-hand side of the PPD 100, and they are lowered on the right-hand side.

Falls do, however, happen even despite the use of bed rails. Such bed rails may even increase the severity of a possible fall in unfavorable cases, because the patient falls from a greater height while attempting to overcome the bed rail. In addition, there is a risk that a patient will be entrapped in the bed rail in an unfavorable manner and suffer injuries as a consequence of this or even dies. Lying on body parts, especially the extremities, over a long period of time may lead to pressure sores, which in turn represent a great health risk themselves. A study (Capezuti, Wagner & Brush, 2007) is also devoted to the subject that bed rails may consequently represent an (increased) risk themselves.

Bed rails can likewise help a patient in turning around in the bed or to change his or her position, because the patient can hold onto them and pull himself or herself along the rails. In addition, they offer the possibility of attaching objects (e.g., drains, urine bags, patient fixing devices, etc.). In any case, the health care staff must weigh thoroughly whether bed rails should be mounted or not. A possible guideline, especially for the U.S.A., for a decision can be found, e.g., in (Talerico & Capezuti, 2001). At least in Germany, there also are legal obstacles to the use of bed rails, since raising them may represent a deprivation of freedom, and a reason for justifying them may be necessary. If a patient is of sound mind, he can offer the reason himself or herself. Otherwise, a physician may order the use of bed rails for up to 24 hours in an emergency situation. It is also allowed in a care situation (e.g., when changing the setting or position of the PPD 100) to raise the bed rails for a short time. Otherwise or beyond this, a judge would have to be consulted if necessary.

The raising of bed rails requires documentation every time. This should include at least the time, the reason and a reference to the approval. Further details in reference to PPDs 100 and also concerning the other aspects explained here, reference is made to the document DE 10 2015 013 031.5 (corresponding to U.S. Pat. No. 10,134,128 (B2)), which deals with the determination of partial segment positions of a PPD 100 based on image data, but does not deal with problem related to a lateral limitation 110.

As is further illustrated in FIG. 1, the device 10 may comprise in other exemplary embodiments a detection device 14 for detecting the optical image data of the patient positioning device 100. The detection device 14 may have one or more sensors, which is/are configured to detect a three-dimensional point cloud as image data, as this is optionally shown in FIG. 1 (optional components are indicated by broken lines in FIG. 1). The detection device 14 may be coupled with a determination device 16 and/or with the interface 12. The detection device 14 may comprise here any one or more optical detection units, detection devices, detection modules, etc. Cameras, image sensors, infrared sensors, sensors for detecting one-, two- or three-dimensional or more-than-three-dimensional data, sensor elements of various types, etc., are conceivable here. The one or more sensors may comprise in other exemplary embodiments at least one sensor that provides at least three-dimensional data. The three-dimensional data accordingly detect information on pixels in the space and may additionally comprise, quasi as additional dimensions, additional information, for example, color information (e.g., red, green, blue (RGB) color space), infrared intensity, transparency information (e.g., alpha values), etc.

There are various types of sensors which, though failing to generate a two-dimensional image of a scenario, do generate a three-dimensional set of points, and comprise, e.g., pixels with coordinates or with different depth information, the information on surface points of an object. For example, information on a distance of the pixels to the sensor or sensor system itself may be present here. There are some sensors that record not only a two-dimensional image, but additionally a depth map, which contains the distance of the individual pixels to the sensor system itself. A three-dimensional point cloud, which represents the recorded scenario in 3D, can then also be calculated from this.

Figure 4:
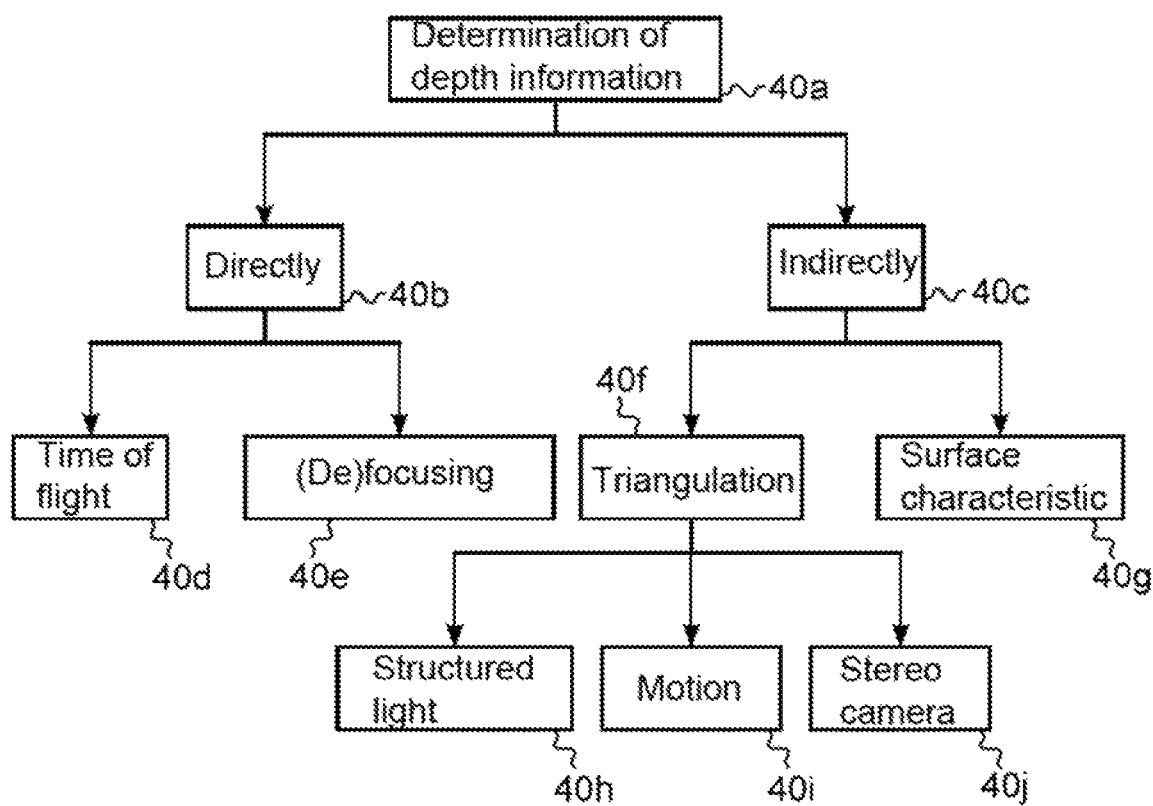
FIG. 4 is an overview diagram for determining three-dimensional image data in some exemplary embodiments.

A review of the different methods for determining the depth information for the depth map is shown in FIG. 4. Distinction can be made between direct and indirect methods, the distance of a point to the system being determined directly by the system itself in the former case and additional processing being necessary in the latter case. Additional information on the individual possibilities can be found, among other things, in (Hartman, 2011). These sensors have been much more favorable and better in the more recent past. The three-dimensional information enables computers to analyze recorded objects more accurately and to derive information of interest, such as distances between objects.

FIG. 4 shows first an overview diagram of the determination of three-dimensional image data in some exemplary embodiments, but determination variants going beyond FIG. 4 may also be used in exemplary embodiments. It should be pointed out that the three-dimensional image data, to which reference is being made here, often correspond to a three-dimensional partial image only, because a sensor only determines pixels from a certain perspective and an incomplete three-dimensional image may thus develop. As will be explained later, a plurality of such partial images may also be combined in order to obtain an image with improved quality or with more pixels, which image may in turn only correspond to a partial image.

FIG. 4 first shows in 40a the determination or calculation of depth information into image data. Direct methods, shown in branch 40b, and indirect methods, shown in branch 40c, can be distinguished, the former determining the distance of a point to the system via the system directly and the latter requiring additional devices for determining the distance. Direct methods are, for example, time of flight measurements 40d and (de)focusing methods 40e. Indirect methods comprise, for example, triangulation 40f (for example, based on structured light 40h, motion 40i or stereo cameras 40j) and analysis of surface characteristics 40g.

Further details of the different possibilities can be found in, for example, Hartman F., 2011, see above. Such sensors became more cost-effective in the past and were improved further and their performance was increased. Three-dimensional information can enable a computer to carry out corresponding analyses of the detected objects and to provide corresponding data.

As a result, exemplary embodiments can provide a data set that indicates at least a partial position of at least one partial segment 120, 120a, 120b, 120c, 120d of a patient positioning device 100 as a partial plane in three-dimensional space. Partial planes can be indicated in some exemplary embodiments as two-dimensional partial planes in three-dimensional space or as one-dimensional partial straight lines in two-dimensional space. The fact that the planes extend in the third dimension at right angles to the two-dimensional coordinates can be assumed to be a higher level of knowledge in the representation of partial straight lines. Reference is made to DE 10 2015 013 031.5 (and to U.S. Pat. No. 10,134,128 (B2)) for further details.

At least some exemplary embodiments provide a process, a computer program and/or a device for providing an indicator of the safety of a patient in a bed configuration as a function of detected positions of at least one lateral limitation 110 and of partial segment positions 120 in an automated manner, in a contactless manner and at least partly without a communication connection between the PPD 100 and a receiving system. This object can be accomplished in some exemplary embodiments both during the daytime and during the night, for example, by means of infrared sensors.

The device 10, as it is shown in FIG. 1, may comprise or use in exemplary embodiments 1 . . . n (n=positive integer) sensors, which operate essentially independently from the lighting conditions visible to humans. The sensors can generate, for example, a 3D point cloud each of the scenario, which can be combined into one point cloud. The sensors may be aligned such that a large part of the patient positioning device 100 to be monitored is located in the field of view.

As is also shown in FIG. 1, the device 10 may further comprise a determination device 16, which is configured to determine the position of the at least one partial segment 120 of the patient positioning device 100 based on the image data. The determination device 16 may further be configured to determine a size and a position of a reclining surface of the patient positioning device 100 based on the position of the at least one partial segment 120 of the patient positioning device 100.

The determination device 16 may be coupled with the interface 12 and with the detection device 14. The determination device 16 may correspond in exemplary embodiments to any controller or processor or a programmable hardware component. For example, the determination device 16 may also be embodied as software, which is programmed for a corresponding hardware component. The determination device 16 may thus be implemented as programmable hardware with correspondingly adapted software. Any type of processors, such as digital signal processors (DSPs) or graphics processors, may be used here. Exemplary embodiments are not limited here to a certain type of processor. Any type of processors or even a plurality of processors are conceivable for implementing the determination device 16. FIG. 1 further illustrates that the determination device 16 may be coupled with the detection device 14 in some exemplary embodiments. For example, the one sensor or the plurality of sensors of the detection device 14 detect at least three-dimensional (partial) image data in such an exemplary embodiment and provide these for the determination device 16, which determines in the image data the patient positioning device 100, the position of the at least one partial segment 120 and of the at least one lateral limitation 110.

In one exemplary embodiment, the determination device 16 is implemented by a processor unit, which is connected to the 1 . . . n sensors, and on which the described process is carried out. There may, furthermore, be communication connections, also embodied via the interface 12, in order to connect the sensors to the processor unit and in order to make it possible to transmit the result of the process to other systems, such as display or documentation systems.

Figure 5:
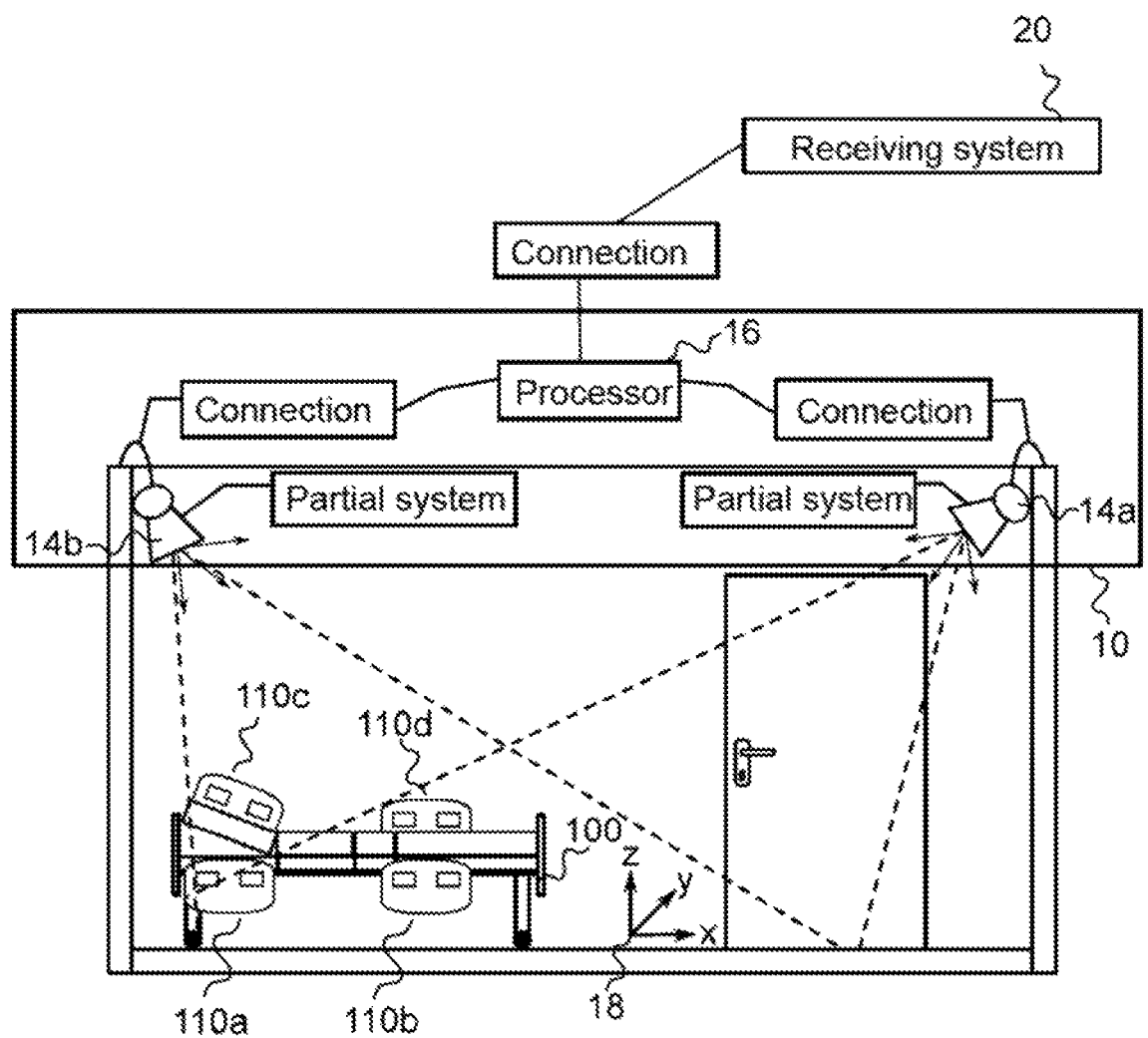
FIG. 5 is a schematic view of an exemplary embodiment in a hospital room.

A conceptual diagram of the device 10 is shown in FIG. 5. FIG. 5 shows an exemplary embodiment in a hospital room. The device 10 comprises here a detection device 14 with two partial systems 14a and 14b for detecting at least three-dimensional partial images from different perspectives of the scenario in the hospital room. FIG. 5 shows, moreover, a configurable hospital bed 100 (representative of a general patient positioning device 100) and a door. The two partial systems 14a and 14b of the detection device 14 are coupled with the determination device 16, which is implemented as a processor unit 16 here, via a communication connection, for example, via Ethernet and Internet Protocol (IP) and/or in a network. FIG. 5 further shows a Cartesian coordinate system 18, on which the following considerations are based.

The device 10 may generally have 1 . . . n sensors, which determine a set of points each, which can be combined or merged into a single three-dimensional (partial) set of pixels. As is shown in the exemplary embodiment in FIG. 5, the detection device 14 may comprise a plurality of image sensors for detecting at least three-dimensional partial image data. The determination device 16 is configured here to combine the data of the plurality of image sensors into image data of an at least three-dimensional partial image of the patient positioning device (here hospital bed) 100 and to carry out the determination of the position of the at least one partial segment 120, 120a, 120b, 120c, 120d based on the (combined) partial image and to determine the position of the at least one lateral limitation 110, 110a, 110b, 110c, 110d based on the position of the at least one partial segment 120, 120a, 120b, 120c, 120d. The combined image data contain, for example, information on the three-dimensional surface of the patient positioning device 100 from the angles of view of the sensors. By the data of a plurality of image sensors being merged, a three-dimensional (partial) image of the hospital bed 100 to be imaged can be generated with a greater degree of detail than with a single image.

The determination device 16, which is configured as a processor unit in the exemplary embodiment shown in FIG. 5, is connected via a network to the 1 . . . n sensors. The actual determination can then be carried out based on the merged data. The network, which can provide a communication connection, may also be used to pass on information on a certain bed configuration, for example, for the purpose of documentation, monitoring or display (e.g., on a monitor or display). FIG. 5 shows a receiving system 20, which may likewise be coupled with the determination device 16 via a communication connection, for example, also via the above-described interface 12. The receiving system 20 receives information on the position of the lateral limitation 110 and processes it further, for example, for documentation, safety monitoring, alarm generation, etc.

The diagram shows two sensors, which observe the scenario and which are connected by a communication connection to the processor unit/computer 16, which executes the described process and is itself connected, in turn, to receiving systems via a communication connection. The diagram contains, furthermore, a schematic bed, as could be used in an intensive care unit. The lateral limitations of the bed are lowered on the side facing the observer and they are raised on the other side.

Figure 6:
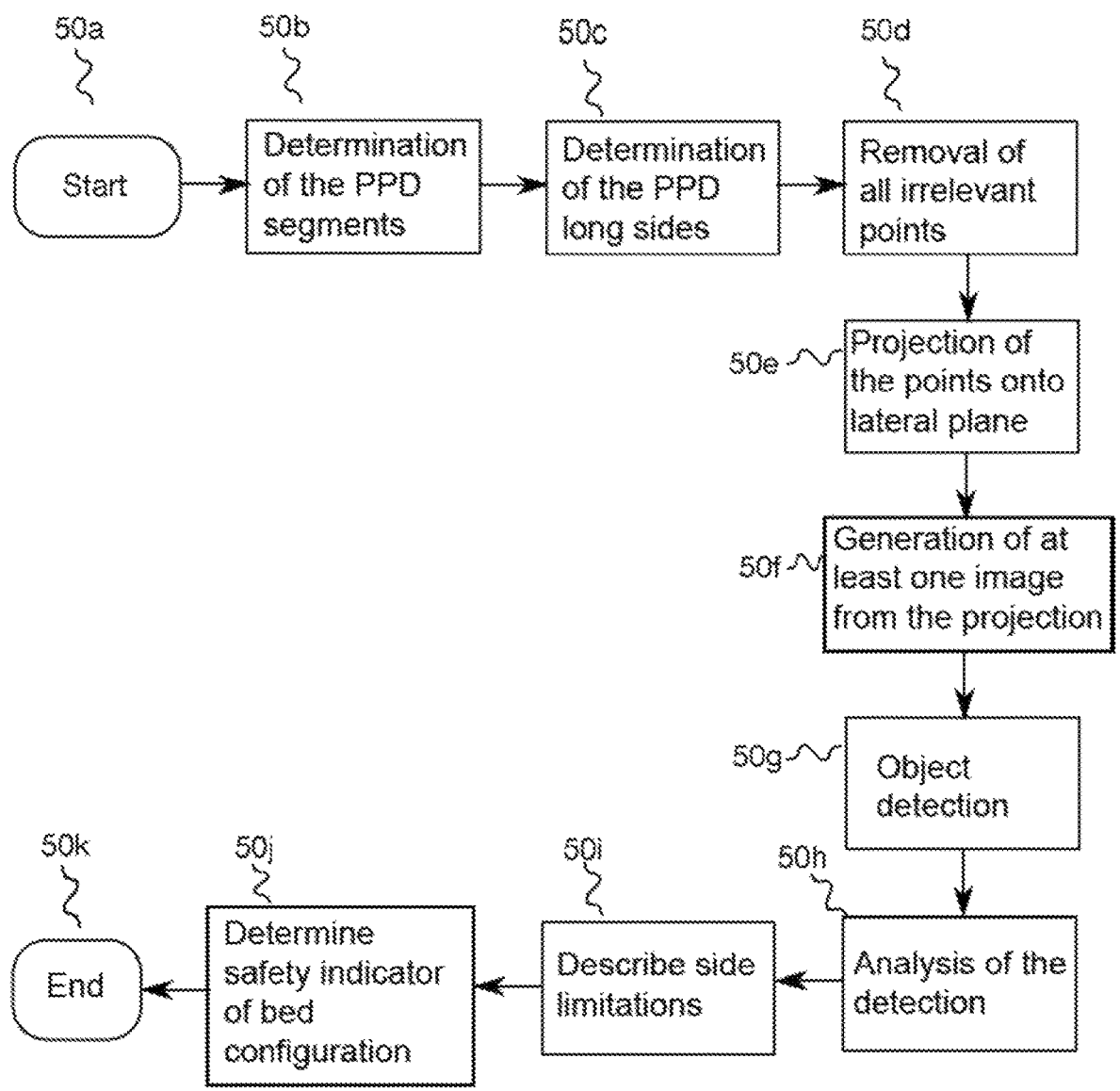
FIG. 6 is a flow chart for determining the position of the lateral limitation in one exemplary embodiment.

A process, which can be executed on a processor unit, is shown in the flow chart in FIG. 6. FIG. 6 shows a flow chart for determining the position of the lateral limitation 110 in an exemplary embodiment. The process waits for a 3D point cloud of the PPD 100, for which the status of the lateral limitations shall be determined, as an input for the starting step 50*a*. This point cloud can be cut out of the entire point cloud of the scenario by object detection and segmentation processes. The process thus begins to describe the reclining surface of the PPD more specifically, i.e., the position (orientation and position) as well as the size of the reclining surface are known, possibly in the form of a plurality of segments 120 to be described, after this executed step, the determination of the PPD segments 50*b*. This step is likewise described in the document DE 10 2015 013 031 (and corresponding U.S. Pat. No. 10,134,128 (B2)).

The determination of the two long sides 50*c* of the PPD is subsequently carried out. The determination device 16 may be configured in some exemplary embodiments to determine two long sides of the patient positioning device 100, and to exclude at least partially pixels that do not belong to the at least one lateral limitation 110 of the patient positioning device 100 from the image data based on the long sides. If present, the lateral limitations 110 are located along the long sides. Based on the information determined up to now, possibly all the points 50*d* that cannot belong to the lateral limitations 110 are now removed, 50*d*. It may also be necessary at this point to divide the remaining points into two subsets, 50*e*, one for each side of the PPD. The determination device 16 is then configured to further limit the image data to pixels of a long side of the patient positioning device 100. The determination device 16 may also be configured to project the image data onto a lateral plane of the patient positioning device 100 and to obtain a projected image.

Steps 50*e*-50*k* pertain to the detection of the lateral limitations 110 of a side of a PPD and are therefore carried out separately for each side with the respective subset of points if the process is to provide information on both sides. The remaining points of the selected subset are then projected onto a lateral plane of the PPD, 50*e*. The process generates from the generated projection in this exemplary embodiment at least one image 50*f*, in which lateral limitations are then searched for by means of object projectors 50*g*. The determination device 16 is configured to determine lateral limitation candidates in the projected image by means of an object detection. The detections performed by the object detectors are subsequently analyzed, 50*h*, and an output 50*i*, which describes the lateral limitations 110, is generated, on the basis of the analysis and the position of the PPD segments 120. The determination device 16 is configured to analyze the lateral limitation candidates and to determine the position of the at least one lateral limitation 110 on the basis of the analyzed lateral limitation candidates.

The automated analysis of the safety of the bed configuration is carried out in the last step 50*j* on the basis of the setting of the lateral limitations and of the segments of the reclining surface, and an alarm is then generated if necessary. The determination device 16 is configured to determine safety information on a configuration of the patient positioning device 100 on the basis of the position of the at least one lateral limitation 110. The determination device 16 may be configured, e.g., to document the safety information by means of a storage device. The determination device 16 may also be configured to output the safety information via a display device, for example, a monitor, a display, a printer, etc. The determination device 16 may further be configured to output alarm information, e.g., optical, haptic or acoustic warning signal for the health care staff based on the safety information if the configuration of the patient positioning device 100 is below a safety level.

Exemplary embodiments can make it possible to document the positions of the lateral limitations 110 and the safety thereof in an automated manner. The safety of a bed configuration can be analyzed in an automated manner for use in further, subsequent algorithms, or for alarm generation. Compared to other processes, which are based on a patient positioning device 100, which is able to detect and communicate the position of the lateral limitations itself, there arises an easier possibility of retrofitting for exemplary embodiments. Exemplary embodiments thus provide a universally usable system, which is not bound to certain patient positioning devices. Exemplary embodiments require no sensor systems arranged at the bed, which may be damaged by, e.g., cleaning procedures or must be encapsulated in a correspondingly complicated manner and at a great expense. If such sensors are present, they can, however, also be used in exemplary embodiments. Status data can always be supplied in a standardized manner even when different PPDs are used in an area. An interfering wiring in the room can also be dispensed with due to processing of the image data. The location and position of the lateral limitation parts in the room become detectable and are available for further processing (e.g., for warning against collision/collision detection).

Some exemplary embodiments will be explained in detail below. Special possible embodiments will be presented for this for the individual process steps described. The determination device can accordingly implement the different steps and detectors. A 3D sensor is used in this exemplary embodiment in order to obtain three-dimensional points, which describe the PPD 100. A commercially available desktop computer may be used as the processor unit 16. At least one possible embodiment will be described in more detail in the further course for each of the steps shown schematically in FIG. 6.

Figure 7:
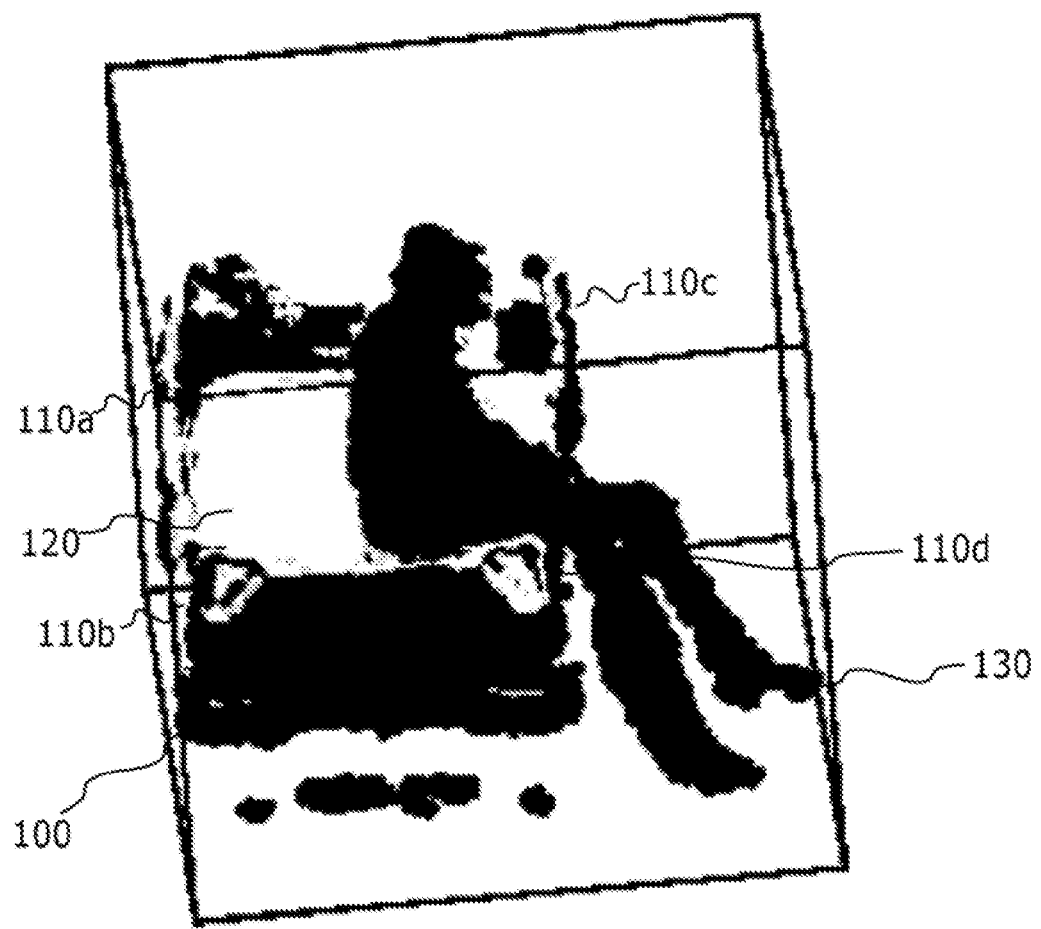
FIG. 7 is a schematic view of detected image data with a bounding box in one exemplary embodiment.

The input point cloud for the process, on the basis of which an exemplary embodiment will be demonstrated, can be seen together with the oriented bounding box (OBB) calculated for the point cloud in FIG. 7. FIG. 7 shows detected image data with a bounding box in an exemplary embodiment. A bed 100 of an intensive care unit, whose segments 120 are set such that they are aligned horizontally with the floor, is shown. A patient 130 is located in a sitting position on the bed. The bed has lateral limitations 110, which comprise two parts per bed side. The two lateral limitations 110 are raised on the left side of the bed 100, and only the bed rail 110 belonging to the head side of the bed 100 is raised on the right side. The OBB for the input point cloud can be determined as a partial result with the process, as it is explained in more detail in the document DE 10 2015 013 031 (and in corresponding U.S. Pat. No. 10,134,128 (B2)).

The reclining surface of the PPD 100 is described in the form of mutually adjustable segments 120 in this exemplary embodiment. These segments can be determined in the form of their size, position and orientation with the processes described in the document DE 10 2015 013 031.5 (and in corresponding U.S. Pat. No. 10,134,128 (B2)).

Figure 8:
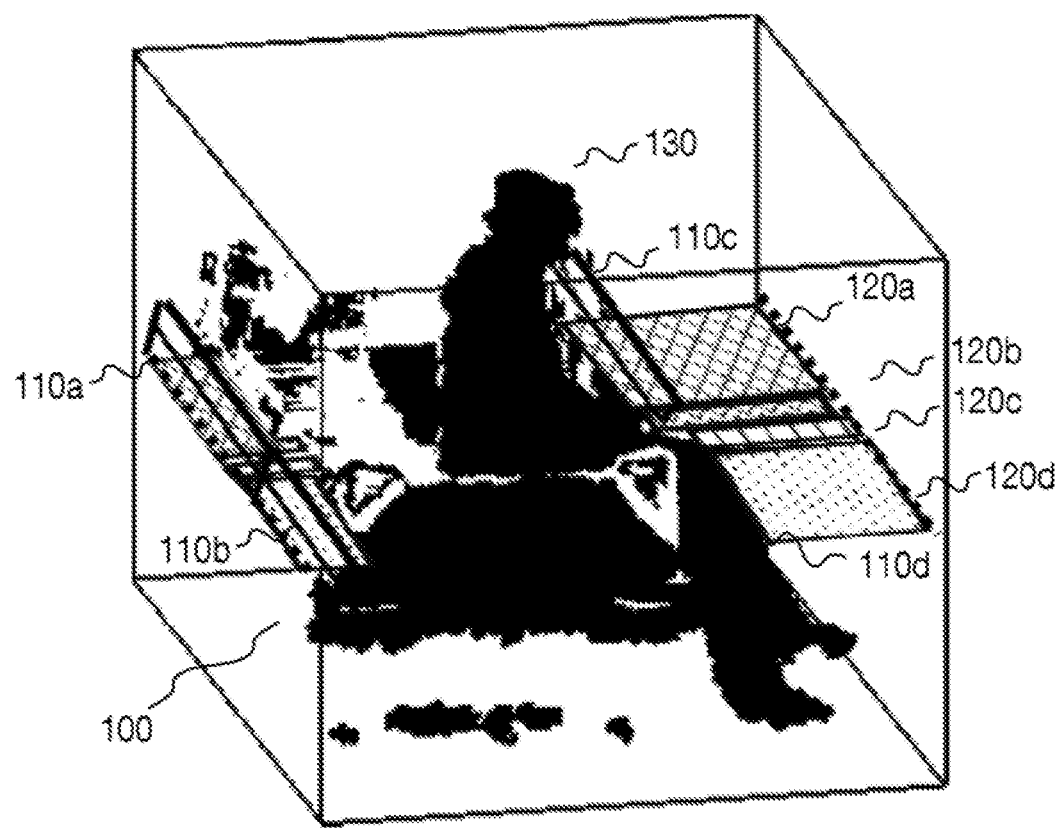
FIG. 8 is a schematic view of detected image data with a bounding box and with determined partial segments in one exemplary embodiment.

FIG. 8 illustrates the detected image data from FIG. 7 with a bounding box and with certain partial segments 120*a*, 120*b*, 120*c*, 120*d* in the exemplary embodiment. The four lateral limitations 110*a*, 110*b*, 110*c*, 110*d* and bed rails can further be seen. FIG. 8 shows the calculated PPD segments 120*a*, 120*b*, 120*c*, 120*d*, which number four in this case, in the input cloud point. As will be seen later, the PPD segments 120*a*, 120*b*, 120*c*, 120*d* are not correct in terms of their size, because the OBB was calculated as being too large based on the sitting person 130. It is therefore impossible in this example to determine the right lateral limitation 110*c*, 110d by looking only in the immediate vicinity of the right-side limitation of the OBB. This is corrected by the following step.

Figure 9:
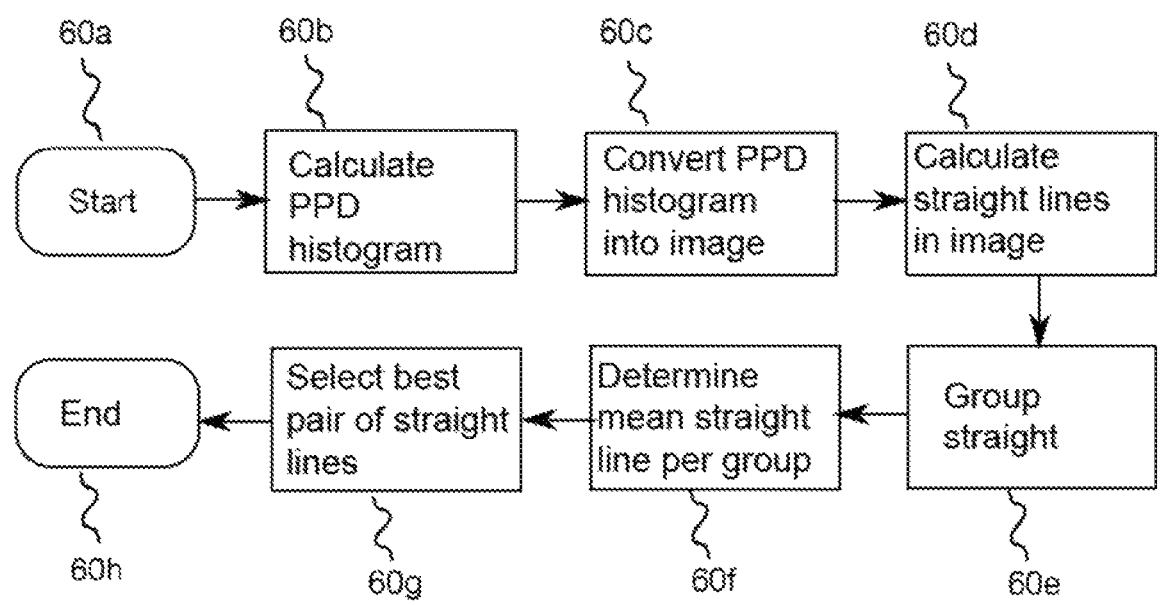
FIG. 9 is a flow chart for determining the lateral limitation in one exemplary embodiment.

To determine the long sides of the PPD 100, at which the lateral limitations 110a-d can potentially be arranged, the procedure described in FIG. 9 is followed in this exemplary embodiment. FIG. 9 shows a flow chart for determining the lateral limitation 110a-d in the exemplary embodiment. The main task of the process is to "cut off" objects projecting on the sides. The basic idea is to generate an image from the input cloud point, in which straight lines are looked for. The pair of straight lines, which best describes the sides of the PPD 100, is then selected and used to determine the long sides. The process begins in step 60a in the exemplary embodiment being considered.

A histogram is first generated, 60b, from the input point cloud, in which the points that are located above one of the rectangles describing the PPD segments 120a-d are projected onto the respective rectangle. A two-dimensional histogram is then generated per segment 120a-d (or rectangle), so that the respective projected points are divided into classes and counted. The histograms are now linked into a single histogram, but the order of the individual histograms (from the foot side to the head side) remains unchanged. It should be noted here that the process has to rely on the PPD segments 120a-d in order to generate the histograms accurately. If, for example, the head segment of the PPD 100 were positioned obliquely, a projection of the points onto the floor plane would not be correct, because the points would now cover a comparatively markedly smaller area in the projection than when the head segment were oriented parallel to the floor. A more robust process is therefore obtained, because the PPD segments 120a-d are used.

Figure 10:
FIG. 10 is an illustration of two histograms in one exemplary embodiment.

In the next step 60c, the process generates an image, which is used for the further process, from the linked histogram. This happens by applying a threshold value to the histogram and by all histogram classes, whose value is above the threshold value, generating a white pixel and all other classes generating a black pixel. Holes in the image are then filled (see Soille, 1999) and an edge image is generated with an edge detector (the literature offers many algorithms for this, e.g., (Canny, 1986). An example is shown in FIG. 10 for both steps. The left side shows the histogram image after filling the holes and the right side the edge image generated therefrom, always for this exemplary embodiment. It can be seen that the two bed sides are located essentially on a straight line, which is interrupted especially by the legs of the patient 130.

The process continues by searching for straight lines 60d in the generated edge image. A possibility of bringing this about is the so-called Hough transformation (Duda & Hart, 1972). The straight lines are shown on the left side of FIG. 11 for the exemplary embodiment being used here. It should be noted that the straight lines are partially so similar to each other that they are located nearly exactly one on top of another and therefore cannot be individually recognized in FIG. 11.

The Hough transformation often finds a plurality of straight lines, which describe each the same side of the bed. The straight lines are grouped for this reason, and each group is later combined into one straight line, 60e. The grouping 60e is carried out by defining a distance between two straight lines and generating a graph based on this. A straight line is represented as a node in this graph and two nodes are connected by an edge if the respective distance of two represented straight lines is smaller than a defined threshold value. The straight lines are now grouped by identifying cliques in the generated graph (e.g., by means of the Bron-Kerbosch algorithm (Bron & Kerbosch, 1973)), wherein a clique corresponds to a group. The distance is based on the slopes of the straight lines and on the points at which they intersect the left edge of the image. All the straight lines found in the process are shown on the left-hand side of FIG. 11, and the remaining mean straight lines are shown on the right-hand side.

Figure 11:
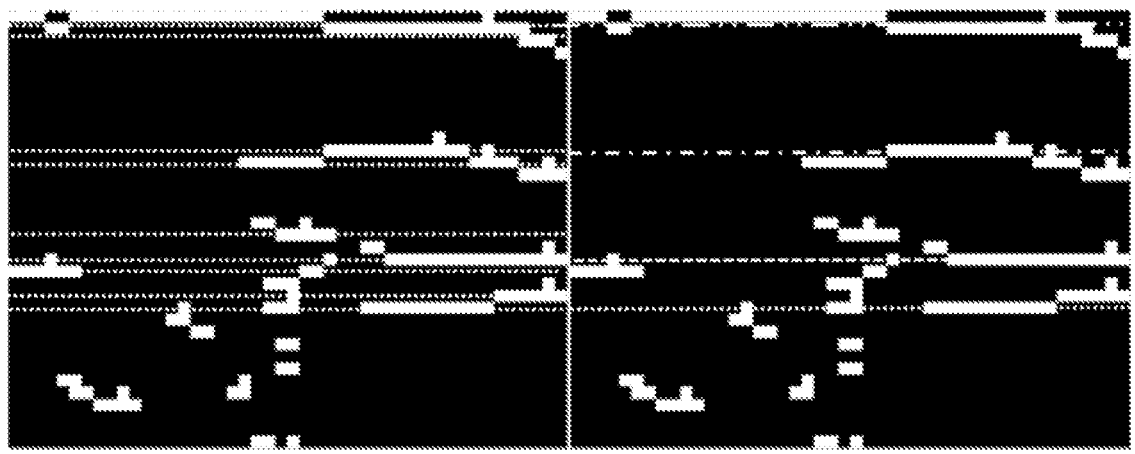
FIG. 11 is an illustration of two histograms in one exemplary embodiment together with found straight lines (left) and with mean straight lines (right)

A representative, averaged straight line is determined per clique found in the next step 60f. This is carried out by taking into account the "straight weight" of the individual straight lines of the group, wherein the straight weight can be defined, for example, as the number of white pixels, which are located close enough to the respective straight line. FIG. 11 shows a mean straight line per identified clique, numbering four in this exemplary embodiment, on the right-hand side. The process then seeks to find the best pair from among the remaining straight lines, 60g. This is carried out by taking into account the slopes of the straight lines (straight lines of a pair shall possibly have a similar slope) as well as he distance between the straight lines, and prior knowledge of the typical width of a PPD 100 may also be included in the latter. The straight lines at the top and at the bottom are thus selected in this exemplary embodiment.

Figure 12:
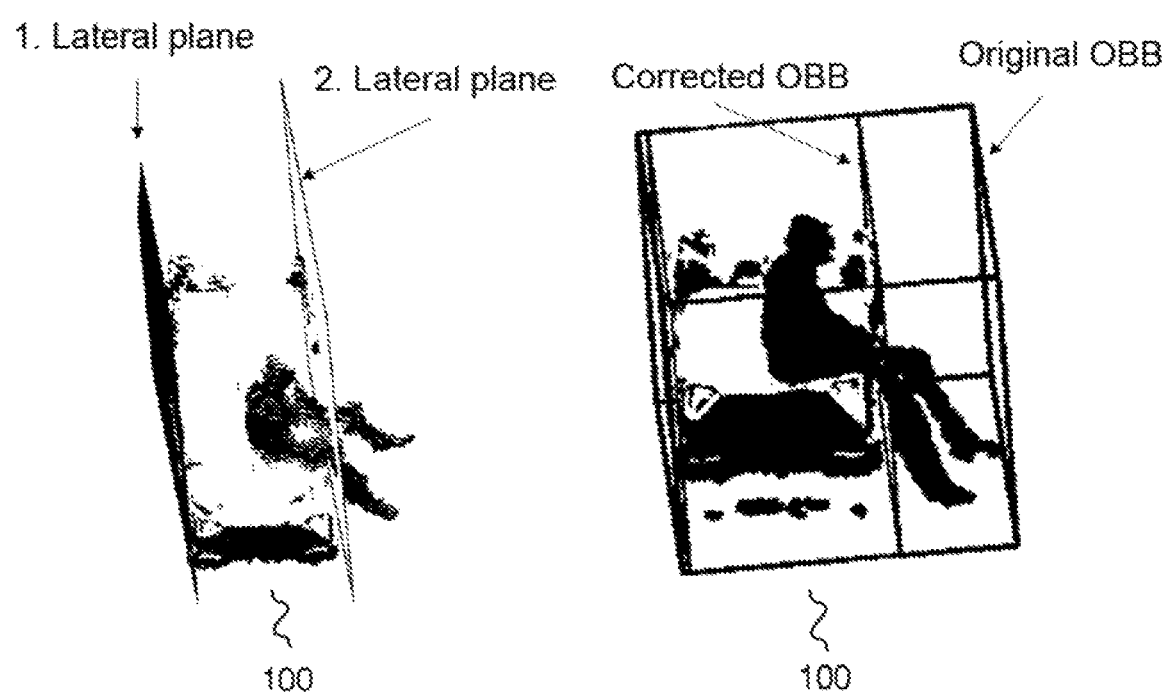
FIG. 12 is a schematic view of bounding boxes obtained on the basis of lateral planes in one exemplary embodiment.

Bounding boxes obtained on the basis of lateral planes in the exemplary embodiment are shown in FIG. 12. The planes obtained from the two straight lines, which planes represent the long sides of the PPD 100, are shown on the left-hand side of FIG. 12. The OBB corrected on this basis is seen on the right-hand side along with the original, incorrect or excessively large OBB. As soon as the long sides of the PPD 100 are determined, possibly all the points that cannot belong to the lateral limitations are removed from the point cloud. Since the lateral limitations extend along the long sides of the PPD 100, all the points that are located between the two lateral planes and are located at a minimum distance (e.g., 10 cm) from these, as well as the points that are not located between two lateral planes and are located at least at a minimum distance (e.g., 10 cm) from both are discarded.

Consequently, all the points that are located at a maximum distance of 10 cm from one of the two planes are maintained in this exemplary embodiment in FIG. 12. These points would contain the long sides of the bed with the lateral limitations as well as a part of the person in the sitting position.

The following steps refer to the determination of the lateral limitation 110 of a PPD side. The left side of the PPD 100 will be considered below in this exemplary embodiment. The division of the remaining points into subsets, one set each for each side of the PPD, is carried out at the distance of the points to the two lateral planes. Points that are located closer to the left-hand lateral plane are assigned to the subset for the left side of the PPD, and all other points are assigned to the subset for the right side of the PPD. The projection, cf. 50e in FIG. 6, onto the left lateral plane itself is to be brought about by means of known mathematical methods.

Similarly to what was described above, an image is generated from the projected points here as well, i.e., a histogram of the points is again calculated, and each histogram class is considered to be a pixel of the image. Using a threshold value, a black-and-white image can then be generated. Filters, especially Gauss filters, can then be applied to the image in order to reduce, e.g., effects that are produced by noise. The result of this exemplary embodiment with the use of a Gauss filter can be seen on the left-hand side of FIG.

Figure 13:
FIG. 13 is an illustration of a projected image in one exemplary embodiment in the knowledge of an orientation of a reclining surface of a patient positioning device.

13. FIG. 13 shows an illustration of a projected image in the exemplary embodiment in the knowledge of an orientation of a reclining surface of a patient positioning device 100. The left-hand part of FIG. 13 shows a generated image of the projected points, and the right-hand side shows the same image in the knowledge of the orientation of the reclining surface in a rotated view.

The two parts of the lateral limitation can be seen, and so can, among other things, the footboard as well. The lateral limitation(s) 110 shall be sought in the next step. To make this step as robust as possible, it may be advisable to keep the variance in the appearances of the lateral limitations 110 as small as possible. The knowledge about the position of the PPD segments 120a-d can be used at this point by rotating the image segment by segment such that the PPD segments 120a-d extend parallel to the horizontal axis of the image. An invariance is thus achieved in relation to adjustments of the PPD segments 120a-d, because the lateral limitations 110 are likewise now aligned parallel to the horizontal axis of the image, which makes additional recordings possible for the object detectors.

The above is true if the lateral limitations 110 are fastened to the PPD segments 120a-d. It also happens, however, that they are mounted at the PPD longitudinal axis, instead. To determine the position and especially the orientation of the longitudinal axis, the following process would be possible, for example:

1) removal of the points that are located only at a maximum of D cm from the floor (these points cannot belong to the PPD longitudinal axis, since the PPDs 100 must, as a rule, guarantee a certain minimum height for the medical staff),
2) removal of the points that are located above the reclining surface (the determined PPD segments 120a-d are needed here),
3) removal of the points that probably belong to the mattress (by removing, for example, points that are located F cm below the respective PPD segments 120a-d), and
4) calculation, based on the remaining points, of a principal component analysis (PCA) (Jolliffe, 2002) and selection of the principal axis as the longitudinal axis of the PPD.

If the orientation of the PPD longitudinal axis is thus known, the image can also be rotated such that this longitudinal axis extends parallel to the horizontal axis of the image. If the type to which the PPD 100 belongs is not known, a plurality of rotated images (rotated taking the PPD segments 120a-d into consideration, rotated on the basis of the longitudinal axis, etc.) can be generated, and lateral limitations 110 can be looked for in this set of images. FIG. 13 shows on the right-hand side the generated image according to the example in a rotated state, so that the PPD segments 120a-d are parallel to the horizontal axis of the image.

Figure 14:
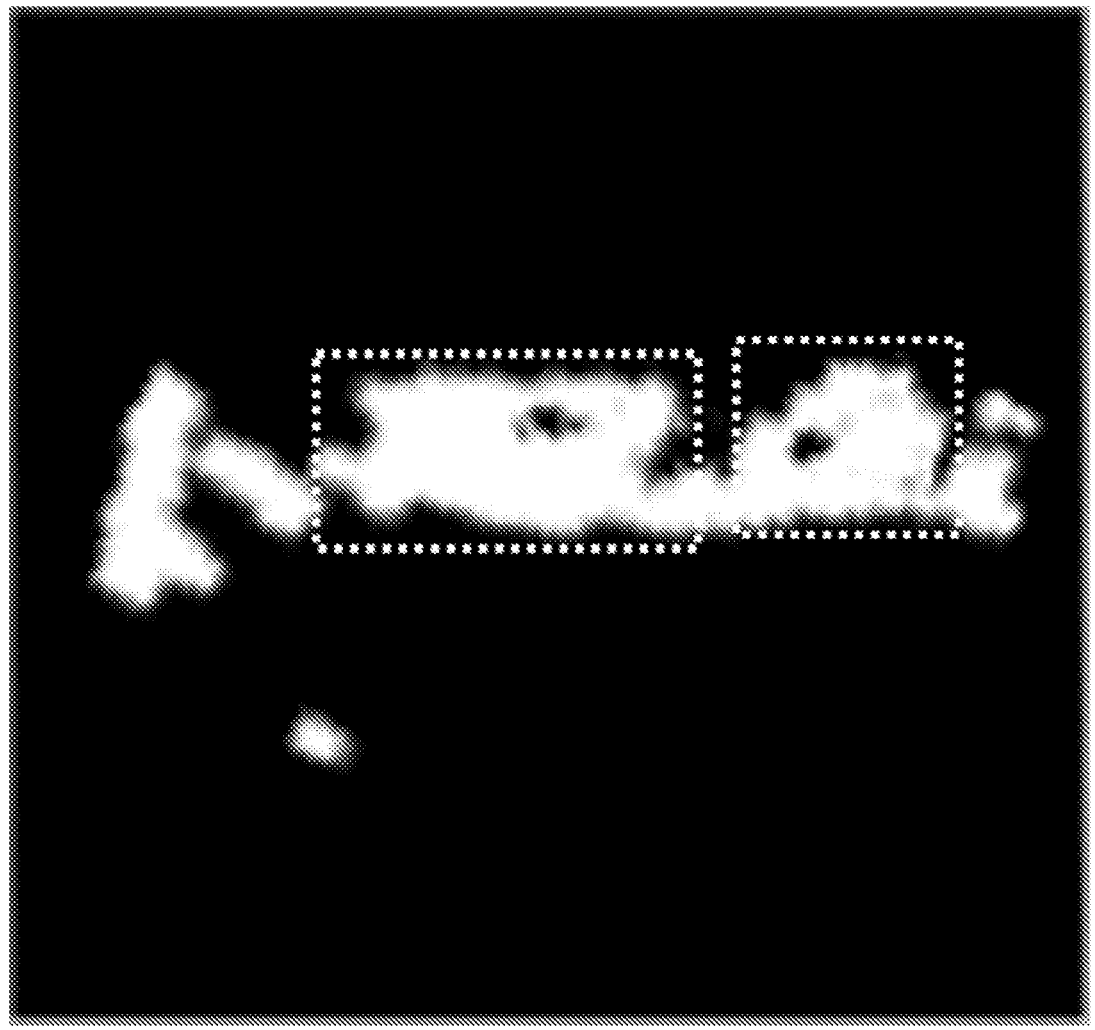
FIG. 14 is an illustration of lateral limitations identified by an object detector in one exemplary embodiment.

Lateral limitations are looked for in the rotated image (FIG. 13, right-hand side) in this exemplary embodiment by using trained object detectors. According to the Viola-Jones algorithm (Viola & Jones, 2001), using HOG features (Dalal & Triggs, 2005, English: Histograms of Oriented Gradients, Histograms, Histogramme orientierter Gradienten), an object detector, which is capable of recognizing lateral limitations in the image, is trained. HOG is a feature that is based on histograms of gradients and the orientation thereof in different image areas. The result of the search of the detector is shown in FIG. 14. FIG. 14 shows partial segments and lateral limitations identified by an object detector in an exemplary embodiment.

The detector has successfully recognized and localized the two parts of the left-hand lateral limitation (recognizable from the broken rectangles in FIG. 14). It should be noted that object detectors according to the Viola-Jones algorithm do not represent the only possibility of localizing the lateral limitations. It would likewise be possible, for example, to scan the image according to a "sliding window" principle. A rectangle ("window") is displaced here in different sizes over the image ("sliding") and a feature vector, on the basis of which a classifier decides whether or not a lateral limitation is located in the rectangle, is determined for each rectangle thus selected. For example, the HOG, which was already mentioned above (Dalal & Triggs, 2005), Local Binary Pattern or Haar features can be used as a feature vector. A combination of these features would be possible as well. A Support Vector Machine or a Random Forest Classifier could be used as classifiers. Further details of these detectors and algorithms can be found, for example, in Ojala, T., M. Pietikainen, and T. Maenpaa, "Multiresolution Gray-scale and Rotation Invariant Texture Classification With Local Binary Patterns." *IEEE Transactions on Pattern Analysis and Machine Intelligence*, Volume 24, No. 7, July 2002, pp. 971-987, Viola, P. and M. J. Jones, "Rapid Object Detection using a Boosted Cascade of Simple Features." *Proceedings of the 2001 IEEE Computer Society Conference*. Volume 1, Apr. 15, 2001, pp. I-511-I-518, Cortes, Corinna and Vladimir Vapnik. "Support vector networks." *Machine learning*, 20.3 (1995): 273-297, and Breiman L. Random forests. In: *Machine Learning*, pp. 5-32, 2001.

It may definitely happen that the object detectors make a plurality of detections, including possibly false ones. A subsequent step, which analyzes the generated set of detections, is therefore appropriate, cf. 50h in FIG. 6. Various conditions are used in this exemplary embodiment in order to analyze and to sort out the detections. Thus, a plurality of lateral limitations cannot, for example, be arranged one on top of another (when viewed from the floor towards the ceiling). The fact that many known processes for object detection, such as the Viola-Jones algorithm as well, indicate a confidence for each detection can be utilized here. For example, only the detection with the highest confidence may thus be retained from among detections made one on top of another. As an alternative or in addition, detections that are arranged under the reclining surface may be preferred. The idea behind this is that interfering objects (e.g., pillows), which may possibly lead to incorrect detections, may be present on the reclining surface. If, however, a lowered lateral limitation is already found in this section of the PPD, the incorrect detections, which can be attributed to the pillow, can be sorted out. The lateral limitations 110 of the PPD 100 comprise one part or more parts per side. The number of detections per side can therefore further be limited to a maximum of two on the basis of the confidence indicators.

The result of the process or the description of the lateral limitations may vary. The configuration of the lateral limitation can first be described, i.e., it is decided on the basis of the detections whether the lateral limitation in question is a one-part or two-part lateral limitation (of course, per side again). Each part can now be further described in terms of its setting, e.g., 1) by a polygon in three-dimensional space,
2) by a cuboid in three-dimensional space, 3) by its mean height above (or under) the reclining surface or the PPD longitudinal axis in the section of the part being considered, and
4) by a number between x (e.g., 0) and y (e.g., 10), wherein x indicates the lowest position and y the highest position of the part. The positions x and y could be known, for example, from the type of the PPD.

It should be noted that the outputs, which provide information on the height of the part of the lateral limitation 110, require a reference point. Especially the surface of the PPD 100 is useful for this, since the height of the lateral limitation above the reclining surface is decisive for the effect of the limitation itself. As was already mentioned above, the determination device 16 may be configured in at least some exemplary embodiments to output alarm generation information on the basis of the safety information or also based on a safety indicator when the configuration of the patient positioning device 100 is below a safety level. For example, the safety level of the patient positioning device 100 may be based on a relative position of the at least one partial segment 120 in relation to the at least one lateral limitation 110.

Figure 15:
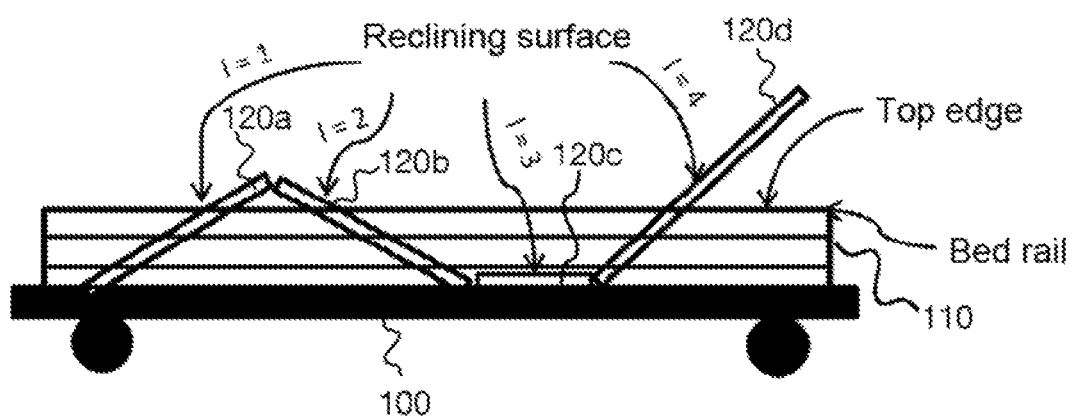
FIG. 15 is a schematic view showing possible configurations of a hospital bed with bed rails in one exemplary embodiment.

As is described in FIG. 6 in step 50*j*, the safety indicator can be determined and interpreted for the bed configuration against the background of the detected settings of the lateral limitations 110 and reclining surface segments 120 of the PPD 100 in order to obtain information on the safety of the current PPD configuration for the patient. The four reclining surfaces (l=1, 2, 3, 4) are arranged above the respective partial segments 120*a-d* in FIG. 15. FIG. 15 illustrates possible configurations of a hospital bed with bed rails 110 in the exemplary embodiment. This information can be obtained in a substantially more knowledgeable manner with the process being presented here in some exemplary embodiments than with a simple binary (raised, lowered) detection. For the explanation, observe, for example, the PPD configuration shown in FIG. 15. The bed rail 110 is raised here, but the configuration is potentially still hazardous; especially due to the raised head segment (l=4) of the reclining surface, a patient is better able in this case despite the bed rail 110 to leave the PPD 100. There is a certain risk of falling.

Based on the known position of the reclining surface segments 120 and of the bed rails 110 and hence the relation thereof to one another, it would be possible to identify such a situation. Some possibilities shall be shown for this below.

Figure 17:
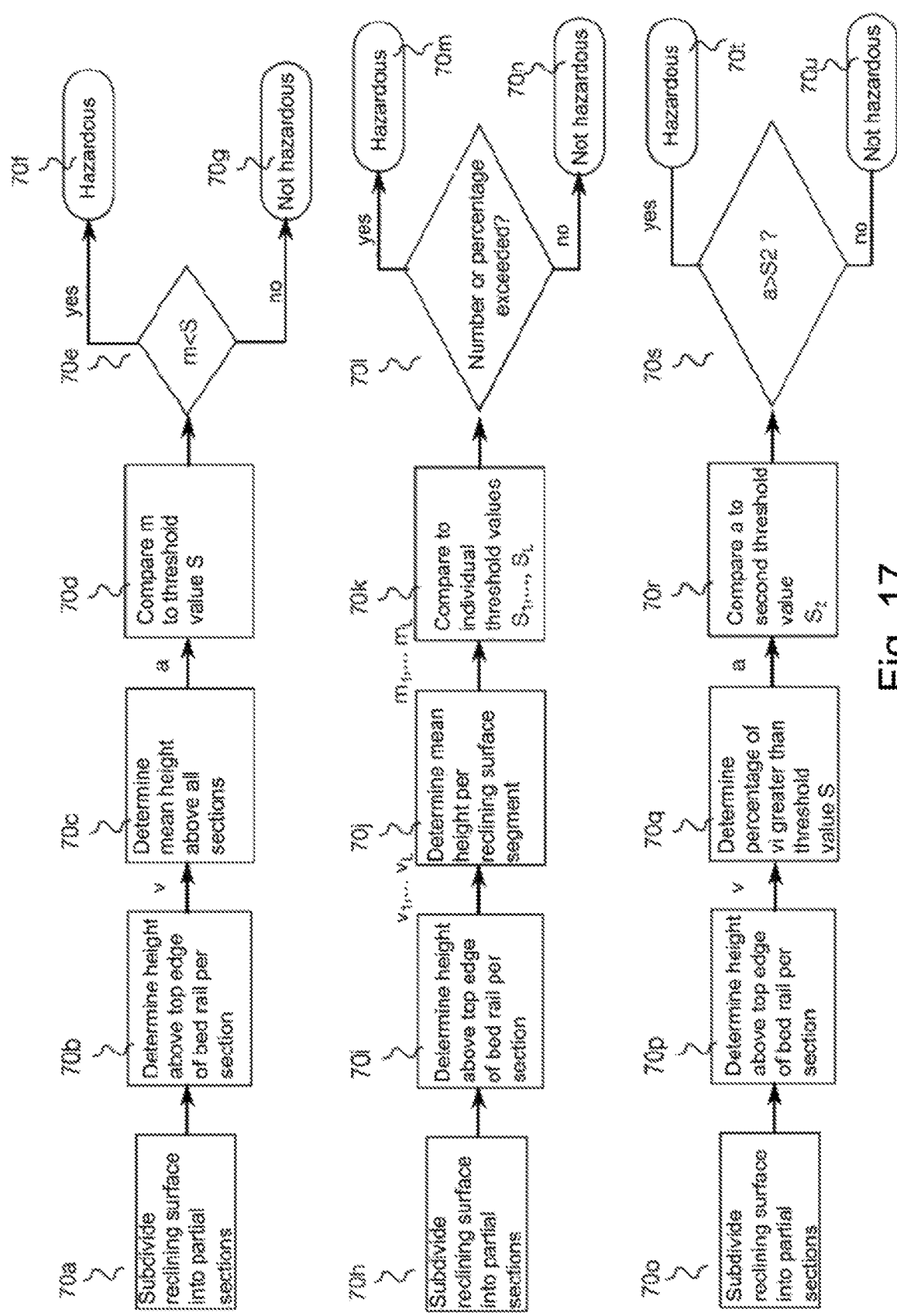
FIG. 17 is a block diagram showing different exemplary embodiments of processes for determining safety information.

Reference is made here to FIG. 17, which shows different exemplary embodiments of processes for determining safety information. FIG. 17 shows "safety indicator flow charts" in the form of flow charts. The mean height above the reclining surface is accordingly determined in some exemplary embodiments. The safety level may represent an indicator of a mean height of the lateral limitation 110 above a reclining surface above the at least one partial segment 120. For example, the reclining surface is first divided into partial sections 70*a* (cf. FIG. 17, upper flow chart). For example, the reclining surface could be divided into pieces measuring 5 cm in length, so that 40 partial sections would be generated for a reclining surface with a length of 2 m. The height above or below the top edge of the bed rail is then determined for each partial section, 70*b*, which would yield a vector $$v = \frac{v_1}{v_{40}}$$

in this case. At 70*c*, the mean height above the reclining surface is then determined via $$m = \frac{1}{40} \sum_{i=1}^{40} v_i.$$

Finally, m is compared to a threshold value S at 70*d*. $v_i$ indicates the height of the reclining surface sections above the top edge of the bed rail, i.e., they are positive if the section is located above the edge and it is otherwise negative. High values of $v_i$ mean risk, which is reflected in step 70*e* by the fact that the threshold value S is exceeded. If the mean height m is smaller than S, the situation is classified as being hazardous, 70*e-f*, and otherwise not, 70*e-g*. Shall the process output a continuous indicator of safety, M=m−S would be a possibility.

A mean height per reclining surface segment 120 can also be determined in some exemplary embodiments, cf. 70*h*, 70*i* in the diagram in the center of FIG. 17. A refined possibility would be to divide the partial sections v according to reclining surface segments, so that a partial section vector is obtained for each reclining surface segment. Consequently, $v_i, \ldots, v_{L-4}$ in this case, with $$v_i = \frac{v_{i1}}{v_{in}}.$$

A mean height can then be calculated individually for each reclining surface segment analogously to the above explanation, 70*j*, so that $m_1, \ldots, m_L$ is obtained. These separate mean heights per reclining surface segment can now be compared to individual threshold values $S_1, \ldots, S_4$. When now comparing the mean heights with their corresponding threshold values mi<$S_i$, 70*k*, information can be obtained on the safety by using the number or the percentage of comparisons yielding positive results, 70*l*, 70*m*, 70*n*. This procedure could make it possible, for example, to define a low threshold value for the head segment, so that an alarm is generated in case of doubt sooner when there is a risk of falling head first.

Figure 16:
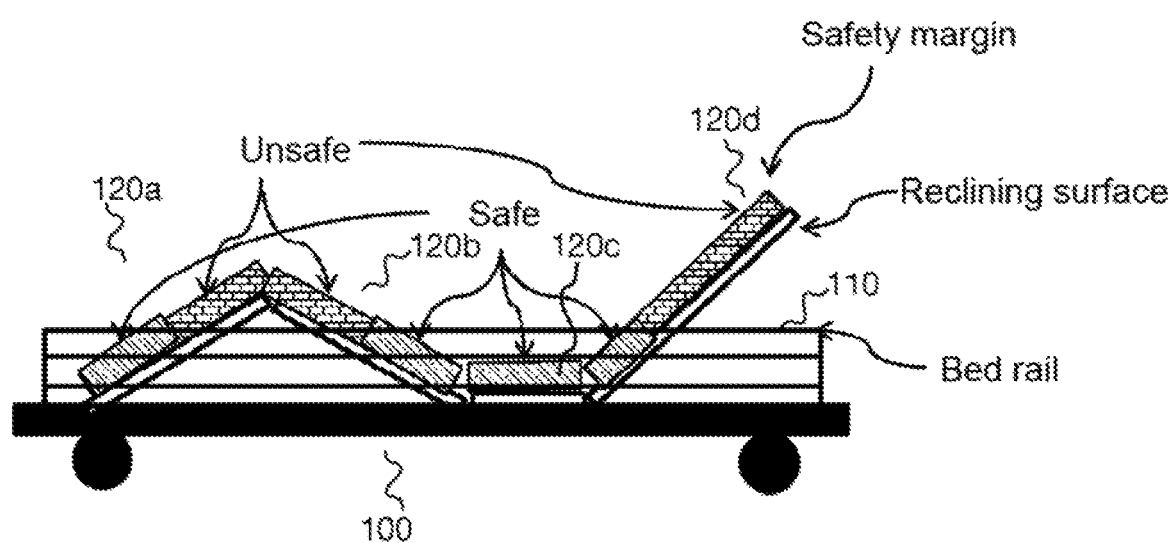
FIG. 16 is a schematic view showing potential analyses in one exemplary embodiment.

It would be possible to determine the percentage of the safe areas in another exemplary embodiment, cf. FIG. 17, flow chart at the bottom, 70*o*, 70*p*. Instead of calculating mean heights, the heights of the top edges of the bed rail, v, above the reclining surface can also be compared directly to one or more threshold values S, 70*q*. A safety margin above the reclining surface is thus defined, in principle, by S. If the top edge of the bed rail is located below this safety margin, corresponding areas are marked as being unsafe. Reference shall be made here to FIG. 16 for clarification. FIG. 16 shows potential analyses in an exemplary embodiment. FIG. 16 illustrates a PPD 100, partial segments 120*a-d* and a bed rail 110. The percentage of the unsafe areas a can now be compared to a second threshold value S2, cf. 70*r*, 70*s*, in order to analyze the safety of the configuration and optionally to generate an alarm.

The above-mentioned possibilities differ mainly in how the partial sections v are formed and analyzed. The flow charts in FIG. 7 show only an analysis as "hazardous" and "nonhazardous," but it is also possible in each case to show a number, which indicates the degree of the risk continuously (as a rule, the distance to the corresponding threshold value). For example, an alarm generation step may then be carried out following this analysis.

Exemplary embodiments can make it possible to document the positions of the lateral limitations 110 and the safety in an automated manner. An indicator can be determined in some exemplary embodiments for the safety of a bed configuration on the basis of the position of the lateral limitations 110 and of the partial segment positions 120 and stored in a documentation system. A documentation system is typically configured as a data bank, in which information on the safety of a bed configuration can be stored. This information may follow different data bank models, e.g., the hierarchic, relational, object-oriented or document-oriented model. These data banks are embedded, for example, in clinical information systems in a medical setting.

Alarm generation may be carried out in some other exemplary embodiments based on the safety information. The determined indicator of the safety of a bed configuration on the basis of the position of the lateral limitations 110 and of the partial segment positions 120 can be used to generate an alarm automatically in case of a corresponding indication. If a process showed in an exemplary embodiment, for example, an indicator M of safety, which indicator decreases the more unsafe a bed configuration is, the health care staff could set a threshold value S, below which an alarm is generated.

A display system may be implemented in other exemplary embodiments. The device 10 could transmit the calculated indicator of the safety of a bed configuration to a remote display system. In addition, the information, on which the indicator is based, i.e., the position of the lateral limitations 110 and the partial segment positions of the reclining surface, could be transmitted. The medical staff could check in this manner the setting remotely, which could be useful, for example, in areas that are critical from a hygienic point of view.

Examples of such display systems would be:
clinical information systems;
stationary display units, such as simple screens, monitors and displays; and
mobile display devices, such as smart phones or tablets, etc.

The data to be displayed could be available, e.g., via a network or a website, could have been stored in a data bank or passed on to a display unit directly (e.g., via HDMI, High Definition Multimedia Interface). A display triggered by the alarm generation would be possible as well. If the system generates an alarm, for example, as explained above, the above-mentioned information could be transmitted to the above-mentioned display systems only thereafter.

Figure 18:
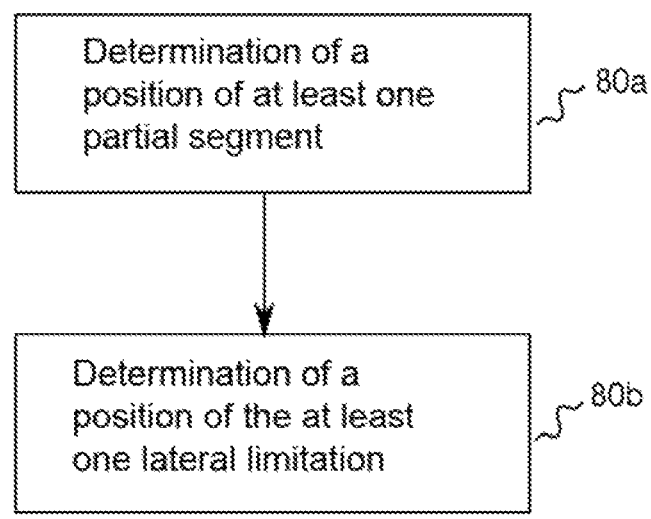
FIG. 18 is a block diagram of a flow chart of an exemplary embodiment of a process for determining a lateral plane.

FIG. 18 shows a block diagram of a flow chart of an exemplary embodiment of a process for determining a lateral plane. The process for detecting optical image data of a patient positioning device 100 and for determining a position of at least one lateral limitation 110 of the patient positioning device 100 based on the image data comprises a determination 80a of a position of at least one partial segment 120 of the patient positioning device 100 based on the image data. The process further comprises the determination 80b of the position of the at least one lateral limitation 110 of the patient positioning device 100 based on the position of the at least one partial segment 120.

Another exemplary embodiment is a program with a program code for executing a process being described here when the program code is executed on a computer, on a processor or on a programmable hardware component.

The features disclosed in the above description, in the claims and in the drawings may be significant for the embodiment of exemplary embodiments in the different configurations thereof both individually and in any combination and, unless something different appears from the description, they may be combined with one another as desired.

Even though some aspects were described in connection with a device, it is obvious that these aspects also represent a description of the corresponding process, so that a block or a component of a device shall also be considered to represent a corresponding process step or a feature of a process step. Analogously to this, aspects that were described in connection with a process step or as a process step also represent a description of a corresponding block or detail or feature of a corresponding device.

Depending on certain implementation requirements, exemplary embodiments of the present invention may be implemented in hardware or in software. The implementation may be carried out with the use of a digital storage medium, for example, a floppy disk, a DVD, a Blu-Ray Disc, a CD, a ROM, a PROM, an EPROM, an EEPROM or a FLASH memory, a hard drive or another magnetic or optical memory, on which electronically readable control signals are stored, which can or do interact with a programmable hardware component such that the process in question is executed.

A programmable hardware component may be formed by a processor, a computer processor (CPU=Central Processing Unit), a graphics processor (GPU=Graphics Processing Unit), a computer, a computer system, an application-specific integrated circuit (ASIC), an integrated circuit (IC), a System on Chip (SOC), a programmable logic element or a field-programmable gate array (FPGA) with a microprocessor.

The digital storage medium may therefore be machine- or computer-readable. Some exemplary embodiments consequently comprise a data storage medium, which has electronically readable control signals, which are capable of interacting with a programmable computer system or with a programmable hardware component such that one of the processes described here is executed. Thus, an exemplary embodiment is a data storage medium (or a digital storage medium or a computer-readable medium), on which the program for executing the processes described here is recorded.

Exemplary embodiments of the present invention may generally be implemented as program, firmware, computer program or computer program product with a program code or as data, wherein the program code or the data act such as to execute one of the processes when the program is running on a processor or on a programmable hardware component. The program code or the data may also be stored, for example, on a machine-readable medium or storage medium. The program code or the data may be present, among other things, as source code, machine code or byte code as well as another intermediate code.

Another exemplary embodiment is, furthermore, a data stream, a signal sequence or a sequence of signals, which data stream or signal sequence represents the program for executing one of the processes being described here. The data stream, the signal sequence or the sequence of signals may be configured, for example, such as to be transferred via a data communication connection, for example, via the Internet or another network. Exemplary embodiments are thus also signal sequences representing data, which signal sequences are suitable for transmission via a network or a data communication protocol, wherein the data represent the program.

A program according to an exemplary embodiment may implement one of the processes while it is executed, for example, by reading storage locations or writing a datum or a plurality of data into these, as a result of which switching operations or other processes are possibly elicited in transistor structures, in amplifier structures or in other electrical, optical, magnetic components or in components operating according to another principle of function. By reading a storage location, data, values, sensor values or other information can correspondingly be detected, determined or measured. A program can therefore detect, determine or measure variables, values, measured variables and other information by reading from one or more storage locations and bring about, trigger or execute an action as well as actuate other devices, machines and components by writing to one or more storage locations.

The above-described exemplary embodiments present only an illustration of the principles of the present invention. It is obvious that modifications and variations of the arrangements and details described here may be obvious to other persons skilled in the art. The present invention is therefore intended to be limited only by the scope of protection of the following patent claims rather than by the specific details that are presented here on the basis of the description and the explanation of the exemplary embodiments.

While specific embodiments of the invention have been shown and described in detail to illustrate the application of the principles of the invention, it will be understood that the invention may be embodied otherwise without departing from such principles.

The invention claimed is:

1. A device for detecting optical image data of a patient positioning device and for determining a position of at least one lateral limitation of the patient positioning device based on the image data, the device comprising,
    a determination device configured to determine first a position of at least one partial segment of the patient positioning device based on the image data, and to determine the position of the at least one lateral limitation of the patient positioning device on the basis of the position of the at least one partial segment, and to determine safety information on a configuration of the patient positioning device based on the position of the at least one lateral limitation, and to output alarm generation information based on the safety information when the configuration of the patient positioning device is below a safety level, the safety level being based on the position of the at least one lateral limitation relative to the position of the at least one partial segment,
    wherein the determination device is further configured to determine a size and a position of a reclining surface of the patient positioning device based on the position of the at least one partial segment of the patient positioning device,
    wherein the determination device is further configured to determine two long sides of the patient positioning device, and to at least partially exclude from the image data, based on the long sides, pixels that do not belong to the at least one lateral limitation of the patient positioning device based on the long sides.

2. A device in accordance with claim 1, further comprising an interface for outputting information on the position of the at least one lateral limitation, the at least one partial segment comprising a surface for supporting a patient, the at least one lateral limitation being located adjacent to the at least one partial segment.

3. A device in accordance with claim 1, further comprising a detection device for detecting the optical image data of the patient positioning device, wherein the detection device has one or more sensors, which is/are configured to detect a three-dimensional point cloud as image data.

4. A device in accordance with claim 1, wherein the determination device is configured to limit the image further to pixels of a long side of the patient positioning device.

5. A device in accordance with claim 4, wherein the determination device is configured to project the image data onto a lateral plane of the patient positioning device and to obtain a projected image.

6. A device in accordance with claim 5, wherein the determination device is configured to determine lateral limitation candidates in the projected image by means of an object detection.

7. A device in accordance with claim 6, wherein the determination device is configured to analyze the lateral limitation candidates and to determine the position of the at least one lateral limitation on the basis of the analyzed lateral limitation candidates.

8. A device in accordance with claim 1, wherein the determination device is configured to document the safety information via a storage device.

9. A device in accordance with claim 1, wherein the determination device is configured to output the safety information via a display device.

10. A device in accordance with claim 1, wherein the safety level of the patient positioning device is based on a relative position of the at least one partial segment in relation to the at least one lateral limitation.

11. A device in accordance with claim 1, wherein the safety level represents an indicator of how high is a risk of a patient falling out of the patient positioning device in case of the particular configuration of the patient positioning device.

12. A device in accordance with claim 1, wherein the safety level is an indicator of a mean height of the lateral limitation above a reclining surface above the at least one partial segment.

13. A device in accordance with claim 1, wherein the determination device is configured to determine the position of at least two partial segments of the patient positioning device.

14. A process for detecting optical image data of a patient positioning device and for determining a position of at least one lateral limitation of the patient positioning device based on the image data, the process comprising the steps of:
    determining a position of at least one partial segment of the patient positioning device based on the image data;
    determining the position of the at least one lateral limitation of the patient positioning device based on the position of the at least one partial segment;
    determining safety information on a configuration of the patient positioning device based on the position of the at least one lateral limitation;
    providing alarm generation information as output based on the safety information when the configuration of the patient positioning device is below a safety level, the safety level being based on the position of the at least one lateral limitation relative to the position of the at least one partial segment;

determining a size and a position of a reclining surface of the patient positioning device based on the position of the at least one partial segment of the patient positioning device; and determining two long sides of the patient positioning device, and at least partially excluding from the image data, based on the long sides, pixels that do not belong to the at least one lateral limitation of the patient positioning device based on the long sides.

15. A process according to claim 14, further comprising a program with program code for executing the process steps at least partially on a computer, on a processor or on a programmable hardware component.

16. A device for detecting optical image data of a patient positioning device and for determining a position of at least one lateral limitation of the patient positioning device based on the image data, the device comprising:

a determination device configured to determine first a position of at least one partial segment of the patient positioning device based on the image data, and to determine the position of the at least one lateral limitation of the patient positioning device on the basis of the position of the at least one partial segment, and to determine safety information on a configuration of the patient positioning device based on the position of the at least one lateral limitation, and to output alarm generation information based on the safety information when the configuration of the patient positioning device is below a safety level, the safety level being based on a height of the at least one lateral limitation relative to a height of the at least one partial segment, wherein the determination device is further configured to determine a size and a position of a reclining surface of the patient positioning device based on the position of the at least one partial segment of the patient positioning device, wherein the determination device is configured further to determine two long sides of the patient positioning device, and to at least partially exclude from the image data, based on the long sides, pixels that do not belong to the at least one lateral limitation of the patient positioning device based on the long sides.

* * * * *